(12) United States Patent
Rigas et al.

(10) Patent No.: US 12,150,752 B2
(45) Date of Patent: Nov. 26, 2024

(54) HYDROGEN BREATH ANALYZER AND BREATH TEST METHOD

(71) Applicants: HETERON BIOTECHNOLOGIES, LLC, Setauket, NY (US); Anastasia Rigas, Setauket, NY (US)

(72) Inventors: Anastasia Rigas, Setauket, NY (US); Nabi Sertac Artan, Brooklyn, NY (US); Kalle Levon, Brooklyn, NY (US); Edward Amoako, Corona, NY (US); Hao-Chun Chiang, Syosset, NY (US)

(73) Assignees: Anastasia Rigas; HETERON BIOTECHNOLOGIES, LLC

( * ) Notice: Subject to any disclaimer, the term of this patent is extended or adjusted under 35 U.S.C. 154(b) by 744 days.

(21) Appl. No.: 17/312,881

(22) PCT Filed: Dec. 10, 2019

(86) PCT No.: PCT/US2019/065544
§ 371 (c)(1),
(2) Date: Jun. 10, 2021

(87) PCT Pub. No.: WO2020/123555
PCT Pub. Date: Jun. 18, 2020

(65) Prior Publication Data
US 2022/0031190 A1    Feb. 3, 2022

Related U.S. Application Data

(60) Provisional application No. 62/777,752, filed on Dec. 10, 2018.

(51) Int. Cl.
*A61B 5/08*        (2006.01)
*A61B 5/00*        (2006.01)
(Continued)

(52) U.S. Cl.
CPC ............. *A61B 5/082* (2013.01); *A61B 5/097* (2013.01); *A61B 5/411* (2013.01); *A61B 5/4255* (2013.01);
(Continued)

(58) Field of Classification Search
CPC .......... A61B 5/08; A61B 5/082; A61B 5/097; A61B 5/411; A61B 5/42; A61B 5/4222;
(Continued)

(56) References Cited

U.S. PATENT DOCUMENTS 3,852,036 A    12/1974   Burroughs et al.
3,953,173 A     4/1976   Obayashi et al.
(Continued)

FOREIGN PATENT DOCUMENTS

CN     109164140 A     1/2019
DE     29902593 U1     7/1999
(Continued)

OTHER PUBLICATIONS

Penner, J.L. et al., Serotyping of Campylobacter jejuni and Campylobacter coli on the Basis of Thermostable Antigens. Eur J Clin Microbial. (1983) 2:378-383.
(Continued)

*Primary Examiner* — Eric F Winakur
*Assistant Examiner* — Abel Seifu Abegaz
(74) *Attorney, Agent, or Firm* — NEXUS LAW PLLC; Leonard Raykinsteen

(57) ABSTRACT

The present invention provides an improved breath analyzer and breath test method to determine the presence of a gastrointestinal disorder in a human subject's digestive tract.

19 Claims, 48 Drawing Sheets

(51) Int. Cl.
*A61B 5/097* (2006.01)
*G01N 27/12* (2006.01)
*G01N 33/497* (2006.01)

(52) U.S. Cl.
CPC .............. *A61B 5/742* (2013.01); *G01N 27/12* (2013.01); *G01N 33/497* (2013.01); *G01N 33/4975* (2024.05)

(58) Field of Classification Search
CPC .. A61B 5/4255; A61B 2010/0087; A61B 5/74
See application file for complete search history.

(56) References Cited

U.S. PATENT DOCUMENTS

| | | | |
|---|---|---|---|
| 4,007,063 A | 2/1977 | Yasuda et al. |
| 4,030,340 A | 6/1977 | Chang |
| 4,140,106 A | 2/1979 | Kirmaier |
| 4,169,369 A | 10/1979 | Chang |
| 4,346,583 A | 8/1982 | Hoogstraat |
| 4,430,191 A | 2/1984 | Sone et al. |
| 4,481,499 A | 11/1984 | Arima et al. |
| 4,753,916 A | 6/1988 | Carcia et al. |
| 4,823,803 A | 4/1989 | Nakamura |
| 4,858,063 A | 8/1989 | Laue et al. |
| 4,895,705 A | 1/1990 | Wrighton et al. |
| 4,947,861 A | 8/1990 | Hamilton |
| 5,037,525 A | 8/1991 | Badwal |
| 5,055,441 A | 10/1991 | Mccarron et al. |
| 5,069,220 A | 12/1991 | Casparie et al. |
| 5,252,292 A | 10/1993 | Hirata et al. |
| 5,331,287 A | 7/1994 | Yamagishi et al. |
| 5,531,225 A | 7/1996 | Nawata et al. |
| 5,546,004 A | 8/1996 | Schmelz |
| 5,624,640 A | 4/1997 | Potthast et al. |
| 5,783,154 A | 7/1998 | Althainz et al. |
| 5,787,885 A | 8/1998 | Lemelson |
| 5,811,662 A | 9/1998 | Williams et al. |
| 5,858,186 A | 1/1999 | Glass |
| 5,869,007 A | 2/1999 | Jang |
| 5,969,231 A | 10/1999 | Qu et al. |
| 5,993,625 A | 11/1999 | Inoue et al. |
| 6,156,346 A | 12/2000 | Chen et al. |
| 6,173,602 B1 | 1/2001 | Moseley |
| 6,173,603 B1 | 1/2001 | Horn |
| 6,186,958 B1 | 2/2001 | Katzman et al. |
| 6,234,006 B1 | 5/2001 | Sunshine et al. |
| 6,319,724 B1 | 11/2001 | Lewis et al. |
| 6,411,905 B1 | 6/2002 | Guoliang et al. |
| 6,467,333 B2 | 10/2002 | Lewis et al. |
| 6,491,643 B2 | 12/2002 | Katzman et al. |
| 6,606,566 B1 | 8/2003 | Sunshine |
| 6,609,068 B2 | 8/2003 | Cranley et al. |
| 6,620,109 B2 | 9/2003 | Hanson |
| 6,660,231 B2 | 12/2003 | Moseley |
| 6,703,241 B1 | 3/2004 | Sunshine et al. |
| 6,723,056 B1 | 4/2004 | Alving et al. |
| 6,730,212 B1 | 5/2004 | Yamagishi et al. |
| 6,767,732 B2 | 7/2004 | Alocilja et al. |
| 6,820,012 B2 | 11/2004 | Sunshine |
| 6,839,636 B1 | 1/2005 | Sunshine et al. |
| 6,841,391 B2 | 1/2005 | Lewis et al. |
| 6,981,947 B2 | 1/2006 | Melker |
| 7,014,612 B2 | 3/2006 | Hubbard et al. |
| 7,017,389 B2 | 3/2006 | Gouma |
| 7,101,340 B1 | 9/2006 | Braun |
| 7,104,963 B2 | 9/2006 | Melker et al. |
| 7,189,360 B1 | 3/2007 | Ho |
| 7,220,387 B2 | 5/2007 | Flaherty et al. |
| 7,338,454 B2 | 3/2008 | Butler et al. |
| 7,364,551 B2 | 4/2008 | Allen et al. |
| 7,522,040 B2 | 4/2009 | Passmore et al. |
| 7,640,789 B2 | 1/2010 | Kim et al. |
| 7,687,275 B2 | 3/2010 | Burdinski |
| 7,704,214 B2 | 4/2010 | Abraham-Fuchs et al. |
| 7,867,171 B2 | 1/2011 | Ben-Oren et al. |
| 7,950,271 B2 | 5/2011 | Novak et al. |
| 7,981,215 B2 | 7/2011 | Gouma et al. |
| 8,263,002 B1 | 9/2012 | Chow et al. |
| 8,343,484 B2 | 1/2013 | Farmer et al. |
| 8,485,983 B2 | 7/2013 | Gouma et al. |
| 9,289,155 B2 | 3/2016 | Rigas et al. |
| 9,541,517 B2 | 1/2017 | Samuilov |
| 9,643,186 B1 | 5/2017 | Ahmad et al. |
| 2002/0011569 A1 | 1/2002 | Mori et al. |
| 2002/0090667 A1 | 7/2002 | Ratcliffe et al. |
| 2002/0159950 A1 | 10/2002 | Wagner |
| 2003/0008407 A1 | 1/2003 | Fu |
| 2003/0105407 A1 | 6/2003 | Pearce, Jr. et al. |
| 2003/0175699 A1 | 9/2003 | Tachikawa et al. |
| 2003/0208133 A1 | 11/2003 | Mault |
| 2003/0217586 A1 | 11/2003 | Gouma |
| 2004/0077965 A1 | 4/2004 | Hubbard et al. |
| 2005/0100535 A1 | 5/2005 | Farmer et al. |
| 2005/0129573 A1 | 6/2005 | Gabriel et al. |
| 2005/0171449 A1 | 8/2005 | Suslick et al. |
| 2006/0074335 A1 | 4/2006 | Ben-Oren et al. |
| 2006/0147496 A1 | 7/2006 | Lin et al. |
| 2006/0174385 A1 | 8/2006 | Gruber et al. |
| 2006/0277974 A1 | 12/2006 | Gouma et al. |
| 2007/0048180 A1 | 3/2007 | Gabriel et al. |
| 2007/0048181 A1 | 3/2007 | Chang et al. |
| 2007/0167691 A1 | 7/2007 | Causevic |
| 2007/0209937 A1 | 9/2007 | Hoagland et al. |
| 2007/0256477 A1 | 11/2007 | Moor |
| 2007/0272901 A1 | 11/2007 | Gouma |
| 2008/0053194 A1 | 3/2008 | Ahmad |
| 2008/0077037 A1 | 3/2008 | Gouma et al. |
| 2008/0093226 A1 | 4/2008 | Star et al. |
| 2008/0317636 A1 | 12/2008 | Brahim et al. |
| 2009/0031784 A1 | 2/2009 | Koda et al. |
| 2009/0054799 A1 | 2/2009 | Vrtis et al. |
| 2009/0187111 A1 | 7/2009 | Reilly, Jr. et al. |
| 2009/0266411 A1 | 10/2009 | Habib et al. |
| 2009/0294303 A1 | 12/2009 | Fischer et al. |
| 2010/0006434 A1 | 1/2010 | Virji et al. |
| 2010/0012919 A1 | 1/2010 | Park et al. |
| 2010/0089772 A1 | 4/2010 | Deshusses et al. |
| 2010/0209507 A1 | 8/2010 | Lin et al. |
| 2010/0212403 A1 | 8/2010 | Seal et al. |
| 2010/0215738 A1 | 8/2010 | Ritter et al. |
| 2011/0056846 A1 | 3/2011 | Neethirajan et al. |
| 2011/0061446 A1 | 3/2011 | Gouma et al. |
| 2011/0198240 A1* | 8/2011 | Diaz-Quijada ...... G01N 27/125 205/782 |
| 2011/0259083 A1 | 10/2011 | Lee et al. |
| 2011/0300637 A1 | 12/2011 | Virji et al. |
| 2012/0034646 A1 | 2/2012 | Rigas et al. |
| 2012/0065534 A1 | 3/2012 | Rigas |
| 2012/0186999 A1 | 7/2012 | Walton et al. |
| 2012/0234076 A1 | 9/2012 | Rigas |
| 2012/0237968 A1 | 9/2012 | Rigas |
| 2013/0289368 A1 | 10/2013 | Covington et al. |
| 2014/0221863 A1 | 8/2014 | Rigas |
| 2014/0330153 A1 | 11/2014 | Gouma et al. |
| 2015/0201865 A1 | 7/2015 | Forzani et al. |
| 2015/0250407 A1 | 9/2015 | Rigas |
| 2015/0260706 A1* | 9/2015 | Killard ................ G01N 27/021 436/113 |
| 2016/0097761 A1 | 4/2016 | Sano et al. |
| 2016/0100774 A1* | 4/2016 | Wilcox ................. A61B 5/082 600/532 |
| 2016/0103082 A1 | 4/2016 | Kimura |
| 2017/0105656 A1 | 4/2017 | Rigas |
| 2017/0191953 A1 | 7/2017 | Rigas |
| 2017/0321010 A1 | 11/2017 | Kinlen et al. |
| 2019/0120821 A1* | 4/2019 | Atsalakis ............... A61B 5/087 |
| 2019/0357807 A1 | 11/2019 | Jiang et al. |

FOREIGN PATENT DOCUMENTS

| | | |
|---|---|---|
| JP | 2012202874 A | 10/2012 |
| KR | 101314303 B1 | 10/2013 |
| WO | 0193915 A1 | 12/2001 |

(56) References Cited

FOREIGN PATENT DOCUMENTS

| WO | 0206822 A1 | 1/2002 |
|---|---|---|
| WO | 03041565 A2 | 5/2003 |
| WO | 2009039152 A1 | 3/2009 |
| WO | 2011004567 A1 | 1/2011 |
| WO | 2012125734 A2 | 9/2012 |
| WO | 2012125745 A2 | 9/2012 |
| WO | 2014056961 A1 | 4/2014 |
| WO | 2014063169 A1 | 4/2014 |
| WO | 2015179751 A1 | 11/2015 |
| WO | 2015179755 A1 | 11/2015 |

OTHER PUBLICATIONS

Corazza et al., "Fast Breath Hydrogen in Celiac Disease," Pub Med, Gastroenterology, vol. 93, No. 1, Jul. 1987, pp. 53-58.
Surveyor, Ivor et al., The 14C-urea breath-test for the detection of gastric Campylobacter pylori infection. Med J Aust (1989) 151:435-439.
Hu, Li Tai et al., Purification and N-terminal analysis of urease from Helicobacter pylori. Infect Immun (1990) 58:992-998.
Wang, Xiaodong et al., An integrated array of multiple thin-film metal oxide sensors for quantification of individual components in organic vapor mixtures, Sensors and Actuators B, (1993) 13-14, 458-461.
Murnick, D.E. et al., Laser-Based Analysis of Carbon Isotope Ratios. Science (1994) 263:945-947, retrieved from the Internet on Mar. 22, 2016 at <URL: http://science.sciencemag.org/content/263/5149/945.full-text.pdf+html>.
Cutler, Alan F. et al., Accuracy of invasive and noninvasive tests to diagnose Helicobacter pylori infection, Gastroenterology (1995) 109:136-141, American Gastroenterological Association.
Sberveglieri, G. et al., WO3 sputtered thin films for NOx monitoring, Sensors and Actuators B 26 (1995) pp. 89-92.
Slomianski, Arie et al., [13C]urea breath test to confirm eradication of Helicobacter pylori. Am J Gastroentero. (1995) 90:224-226.
Brandli, 0. et al., Lung function in healthy never smoking adults: reference values and lower limits of normal of a Swiss populatio. Thorax (1996) 51:277-283. Retrieved from the Internet on Mar. 19, 2016 at <http://thorax.bmj.com/>.
Cutler, Alan F., Testing for Helicobacter pylori in clinical practice. Symposium on Helicobacter Pylori, Am J Med (1996) 100:35S-41S, Supplement 5 [Discussion pp. 39S-41S].
Harris, Adam et al., Treating Helicobacter pylori—the best is yet to come? Gut (1996) 39:781-783, retrieved from the Internet on Mar. 19, 2016 at <URL: http://gut.bmj.com/>. Published by group.bmj.com.
Klein, Peter O. et al., Noninvasive detection of Helicobacter pylori infection in clinical practice: the 13C urea breath test. Am J Gastroentero. (1996) 91:690-694.
Mutschall, D., et al., Sputtered molybdenum oxide thin films for NH3 detection 1996 Sensor and Actuators B35-36, p. 320-324.
Dunn, B.E. et al., Helicobacter pylori. Clinical Microbiology Reviews (1997) pp. 720-741, vol. 10, Issue 4, retrieved from the Internet on Mar. 19, 2016 at <URL: http://cmr.asm.org/>.
Monteiro, Lurdes et al., Evaluation of performances of three DNA enzyme immunoassays for detection of Helicobacter pylori PCR products from biopsy specimens. J Clin Microbiol. (1997) 35:2931-2936.
Gouma, P.I. et al., Microstructural Characterization of Sensors based on Electronic Ceramic Materials, JOM, 50 (11), presented as JOM-e., Nov. 1998, 15 pages.
Humerfelt, S., et al., Forced expiratory volume in 1 second (FEV1) and forced vital capacity (FVC) variability in asymptomatic neversmoking men. Clin Physio. (1998) 18:387-396.
Chung, Yong-Keun et al., Gas sensing properties of WO3 thick film for NO2 gas dependent on process condition, Sensors and Actuators B: Chemical (1999) 60:49-56 <doi: 10.1016/S0925-4005(99)00243-9>.

Dutta, Prabir, et al., Interaction of Carbon Monoxide with Anatase Surfaces at High Temperatures: Optimization of a Carbon Monoxide Sensor, J. Phys. Chem. B., 103, pp. 4412-4419, (1999).
Eslick, G.D. et al., Association of Helicobacter pylori infection with gastric carcinoma: a meta-analysis. Am J Gastroenterol (1999) 94:(9) 2373-2379.
Ferroni, A. et al., Nanosized thin films of tungsten-titanium mixed oxides as gas sensors, Sensors and Actuators B 58 (1999) pp. 289-294.
Gouma, P.I. et al., Structural Stability of Titania Thin Films, Nanostructured Materials (1999) 11(8), pp. 1231-1237.
Alcoscan AI2000 Alcohol Breath Analyzer, Craig Medical Distribution Inc., 3 pages, retrieved from Internet on 3/29/3026 at <URL: http://www.craigmedical.com/alcoscan_AL_2000.htm.
Gouma, Pelagia I. et al., Fabrication of Free-Standing Titania-Based Gas Sensors by the Oxidation of Metallic Titanium Foils. J. Am Ceramic. Soc., 83(4), pp. 1007-1009, 2000.
Imawan, C., et al., Gas-sensing characteristics of modified-MoO2 thin films using Ti-overlayers for NH3 gas sensors, Sensors and Actuators B. 64 (2000) pp. 193-197.
Xu, C.N. et al., Selective detection of NH over NO in combustion exhausts by using Au and MoO3 doubly promoted WO element. Sensors and Actuators B, (2000) 65, pp. 163-165.
Abdel-Saheb, Ibrahim, Memorandum: Review of Urea, as an Active and Inert Ingredient Environmental Protection Agency, (2001) Retrieved from Internet on Apr. 1, 2016 at <URL: http://web.archive.org/web/20040722194412/http://www.epa.gov/oppsrrd1/reregistration/urea/UreaEnviron.pdf> 14 pages.
Casellas et al., "Hydrogen Breath Test with D-Xylose for Celiac Disease Screening Is as Useful in the Elderly as in Other Age Groups," Digestive Deseases and Sciences, Oct. 2001, vol. 46, No. 10, pp. 2201-2205.
Eshun, J.K. et al., Comparison of immunohistochemistry and silver stain for the diagnosis of pediatric Helicobacter pylori infection in urease-negative gastric biopsies. Pediatr Dev Patho (2001) 4:82-88.
Guidi, V. et al., Nanosized Ti-doped Mo03 thin films for gas-sensing application. Sens and Act B, (2001) 77:555-560.
Imawan, C.et al., A new preparation method for sputtered MoO3 multilayers for the application in gas layers, Sensors and Actuators B. 78 (2001) pp. 119-125.
Kharitonov, Sergei A. et al., Exhaled markers of pulmonary disease. Am J Respir Crit Care Med (2001) 163:1693-1722.
Livage, Jacques et al., Encapsulation of biomolecules in silica gels. J. Phys.: Condens. Matter 13 (2001) pp. R673- R691, retrieved from the Internet on Mar. 20, 2016 at <URL: http://iopscience.iop.org/.
Marquis, Brent T. et al., A semiconducting metal oxide sensor array for the detection of NOx and NH3, Sensors and Actuators B 77 (2001) pp. 100-110.
Dai, Liming, et al., Sensors and sensor arrays based on conjugated polymers and carbon nanotubes; Pure App. Chem., vol. 74, No. 9, pp. 1753-1772, 2002.
Go, M.F. Review article: natural history and epidemiology of Helicobacter pylori infection. Aliment Pharmacol Ther 16 Suppl (2002) 1:3-15.
Kato, Seiichi et al., Diagnostic Accuracy of the 13C-Urea Breath Test for Childhood Helicobacter pylori Infection: A Multicenter Japanese Study The American J of Gastroenterology, (2002) 97(7):1668-1673.
Kearney, David J. et al., Breath Ammonia Measurement in Helicobacter pylori Infection, Dig Dis Sci (2002) 47:2523-2530.
Leong, R.W. et al., Review article: *Helicobacter* species and hepatobiliary diseases. Aliment Pharmacal Ther (2002) 16:1037-1045.
Phillips, Michael, Detection of Volatile Organic Compounds in Breath. In "Disease markers in exhaled breath" eds Marczin N. Kharitonov SA, Yacoub MH and Barnes PJ. Marcel Decker. (2002) pp. 219-231, New York.
Stejskal, J., Polyaniline. Preparation of a Conducting Polymer (IUPAC Technical Report). Pure Appl. Chem., (2002) vol. 74, No. 5, pp. 857-867, International Union of Pure and Applied Chemistry.
Gatta, L. et al., A rapid, low-dose, 13C-urea tablet for the detection of Helicobacter pylori infection before and after treatment. Aliment Pharmacal Ther (2003) 17:793-798.

(56) References Cited

OTHER PUBLICATIONS

Prasad, A.K. et al., Comparison of solgel and ion beam deposited MoO3 thin film gas sensors for selective ammonia detection. Sens Actuators B. (2003) 93:25-30.
Prasad, A.K., et al., Reactivity sputtered Mo03 films for ammonia sensing. Thin Solid Films (2003) 436:46-51.
Versalovic, James, Helicobacter pylori. Pathology and diagnostic strategies. Am J Clin Patho (2003) 119:403-412. Retrieved from the Internet on Mar. 22, 2016 at <URL: http://ajcp.oxfordjournals.org>.
Gisbert, J.P. et al., Review article: 13C-urea breath test in the diagnosis of Helicobacter pylori infection a critical review. Aliment Pharmacal Ther (2004) 20:1001-1017.
Gouma, P. et al., Novel Materials and Applications of Electronic Noses and Tongues; MRS. Bulletin, Oct. 2004, pp. 697-702.
Graham, D.Y., et al., Challenge model for Helicobacter pylori infection in human volunteers. Gut (2004) 53:1235-1243, retrieved the Internet on Mar. 19, 2016 at <URL: http://gut.bmj.com/>. Published by group.bmj.com.
Pardo, Matteo et al., Electronic Olfactory Systems Based on Metal Oxide Semiconductor Sensor Arrays. MRS Bulletin, Oct. 2004, pp. 703-708, Materials Research Society http://www.mrs.org/publications/.
International Patent Application No. PCT/US2019/065544, International Search Report and Written Opinion mailed Feb. 11, 2020, 9 pages.
Ryan, M.A. et al., PolymerCarbon Black Composite Sensors in an Electronic Nose for Air-Quality Monitoring; MRS Bulletin, Oct. 2004, pp. 714-719.
Suslick, Kenneth S., an Optoelectronic Nose: "Seeing" Smells by Means of Colorimetric Sensor Arrays; MRS Bulletin, Oct. 2004, pp. 720-725, Materials Research Society http://www.mrs.org/publications/.
Winquist, F. et al., Electronic Tongues. MRS Bulletin, Oct. 2004, pp. 726-731, Materials Research Society http://www.mrs.org/publications/.
Agha et al., "Evidence-based examination of the African enigma in relation to Helicobacter pylori infection," Scandinavian Journal of Gastroenterology (2005) 40:523-529, Taylor & Francis Group Ltd, United Kingdom.
Chen, Jyh-Cherng et al., Removal of carbon dioxide by a spray dryer, Chemosphere, (2005) 59:99-105, <doi: 10.1016/i.chemosphere. 2004.09.076>.
Delaney, B., et al., Review article: Helicobacter pylori and gastroesophageal reflux disease. Aliment Pharmscol Ther (2005) 22 Suppl 1 :32-40.
Di Francesco, F., et al., Breath analysis: trends in techniques and clinical applications. Microchemical Journal (2005) 79:105-410.
Sadek et al., "A Room Temperature Polyaniline Nanofiber Hydrogen Gas Sensor," Sensor Technology Laboratory, RMIT University, 2005 IEEE, pp. 207-210.
Timmer, Bjorn et al., Ammonia sensors and their applicationsa review. Sensors and Actuators B, 2005, 107:666-677.
Vaira, Dino et al., Peptic ulcer and Helicobacter pylori: update on testing and treatment. Postgrad Med (2005) 117:17-22, 46. Retrieved from the Internet on Mar. 22, 2016 at <URL: http://dx.doi.org/10.3810/pgm.2005.06.1654> Taylor & Francis Ltd.
Gisbert, J.P. et al., Accuracy of Helicobacter pylori Diagnostic Tests in Patients with Bleeding Peptic Ulcer: A Systematic Review and Meta-analysis. Am J Gastroenterol (2006) 101:848-863.
Gouma, P.I. et al., Selective nanoprobes for 'signalling gases', Nanotechnology 17 (2006) S48-S53, retrieved from the Internet on Mar. 19, 2016 at <URL: http://iopscience.iop.org/article/10.1088/0957-4484/17/4/008/meta; isessionid=DEE5CDBA0DD81DDF45C9D0CA79F53344.c3>.
Helmus, Michael N., et al., Nanotechnology-enabled chemical sensors and biosensors. American Laboratory (2006) 38:34-38.
Murakami, Kazunari et al., Latest insights into the effects of Helicobacter pylori infection on gastric carcinogenesis. World J Gastroentero. (2006) 12:2713-2720.

Papatheodoridis, George V. et al., Effects of Helicobacter pylori and nonsteroidal anti-inflammatory drugs on peptic ulcer disease: a systematic review. Clin Gastroenterol Hepato. (2006) 4:130-142.
Sadek et al., "Polyaniline Nanofiber Based Surface Acoustic Wave Gas Sensors Effect of Nanofiber Diameter on H2 Response," IEEE Sensors Journal, vol. 7, No. 2, Feb. 2007, pp. 213-218.
Tveito, Kari et al., 13C-xylose and 14C-xylose breath tests for the diagnosis of coeliac disease. Scandinavian J. Gastroenterol 2008; 43(2): 166-763. SUNY State University of New York, Stony Brook. Taylor & Francis Ltd.
Waghuley et al., "Application of chemically synthesized conducting polymer-polypyrrole as a carbon dioxide gas sensor," Sensors and Actuators B, vol. 128, 2008, pp. 366-373.
He, Lifang et al., Gas Sensors for ammonia detection based on polyaniline-coated multi-wall carbon nanotubes (2009) Materials Science and Engineering B, 163:76-81.
Rana et al., "Influence of Previously Ingested Wheat on Fasting Breath Hydrogen in Celiac Patients," Dig. Dis. Sci., vol. 54, No. 6, 2009, pp. 1276-1279.
Hryniuk, Alexa et al., A Preliminary Investigation of Exhaled Breath from Patients with Celiac Disease Using Selected Ion Flow Tube Mass Spectrometry. J Gastrointestin Liver Dis. (2010) 19(1) pp. 15-20, Lakehead University , Thunder Bay, Ontario, Canada.
Lupan et al., "Selective hydrogen gas nanosensor using individual ZnO nanowire with fast response at room temperature," Sensors and Actuators B vol. 144, 2010, pp. 56-66.
*Nanomedicon, LLC* v. *Research Found. Of State Univ. of N.Y.*, 2012 NY slip Op 33742(U), Mar. 15, 2012, Supreme Court, Suffolk County, Judge: Emily Pines, 14 pages.
Biesiekierski, Jessica R. et al., No Effects of Gluten in Patients With Self-Reported Non-Celiac Gluten Sensitivity After Dietary Reduction of Fermentable, Poorly Absorbed, Short-Chain Carboydrates. Gastroenterology (2013) vol. 145, 12 pages.
Osorio-Fuente et al., "Submicrometric Fibrillar Structures of Codoped Polyaniline Obtained by Co-oxidation Using te NaClO/Ammonium Peroxydisulfate System: Synthesis and Characterization," J. Mex. Chem. Soc., vol. 57, No. 4, 2013, pp. 306-313.
Wang et al., "Effect of thermal treatment on conductometric response of hydrogen gas sensors integrated with HCl-doped polyaniline nanofibers," Materials Chemistry and Physics, vol. 144, 2014, pp. 155-161.
Decarbiter®, P.W. Perkins Co., Inc., Safety Data Sheet (Jan. 5, 2015) 4 pages.
Giner Electrochemical (trace) Gas Sensors. Datasheet [online]. Giner, In.c, retrieved from the Internet on Apr. 22, 2016 at <URL: http://www.ginerinc.com/products.php?a=TGSI>.
Otsuka America Inc., BreathTek Urea Breath Test, retrieved from the Internet on Mar. 31, 2016 at <http://web.archive.org/web/20120228152952/http://www.otsuka-us.com/Products/Pages/BreathTek.aspx>, 2 pages.
Quest Diagnositics, Helicobacter pylori Urea Breath Test (UBIT), retrieved from the Internet on Mar. 20, 2016 at <URL: http://www.questdiagnostics.com/hcp/topics/gastroent/hpylori_breath.html> 3 pages.
Sultan, et al. "A highly sensitive chlorine gas sensor and enhanced thermal DC electrical conductivity from polypyrrole/silicon carbide nanocomposites," RSC advances 6.87 (Aug. 29, 2016: 84200-84208. Abstract, p. 3 para 2; and p. 12 para 2.
Brown, L.M. Helicobacter pylori: epidemiology and routes of transmission. Epidemiol Rev (2000) 22:283-297.
Dutta, Ritaban et al., Classification of Ear, Nose and Throat Bacteria Using a Neural-Network-Based Electronic Nose; Mrs Bulletin, Oct. 2004, pp. 709-713, Materials Research Society http://www.mrs.org/publications/.
Gisbert, J.P., The recurrence of Helicobacter pylori infection: incidence and variables influencing it. A critical review. Am J Gastroenterol (2005) 100:2083-2099.
Hunt, R.H., Peptic Ulcer Disease: Defining the Treatment Strategies in the Era of Helicobacter pylori. Am J Gastroentero. (1997) 92:36S-40S; discussion 40S-43S.
Leung, Wai K. Helicobacter pylori and Gastric Neoplasia. Contrib Microbio (2006) 13:66-80.
Minoli, Giorgio et al., A Simplified Urea Breath Test for the Diagnosis of Helicobacter pylori Infection Using the LARA Sys-

(56) References Cited

OTHER PUBLICATIONS tem. Laser Assisted Ratio Analyzer. J Clin Gastroenterol. (1998) 26:264-266; retrieved from the Internet on Mar. 28, 2016 at <URL: http://journals.lww.com/jcge/Abstract/1998/06000/A_Simplified_Urea_Breath_Test_for_the_Diagnosis_of_9.aspx>.

O'Morain, Colm. Role of Helicobacter pylori in functional dyspepsia. World J Gastroentero. (2006) 12:2677-2680.

Romagnuolo, Joseph et al., Using Breath Tests Wisely in a Gastroenterology Practice: An Evidence-Based Review. Am J Gastroentero. (2002) 97: 1113-1126.

Sonnenberg, Amnon et al., The prevalence of Self-Reported Peptic Ulcer in the United States. Am J Public Health (1996) 86:200-205.

Tveito, Kari et al., A novel one-hour 13C-sorbitol breath test versus the H2-sorbitol breath test for assessment of coeliac disease. Scandinavian J. Gastroenterol (2009) 44(7): 813-9. SUNY State University of New York, Stony Brook. Taylor & Francis Ltd.

Weir, Susan, et al., Recurrent Bacteremia Caused by a "Flexispira"-Like Organism in a Patient with X-Linked (Bruton's) Agammaglobulinemia. J Clin Microbio (1999) 37:2439-2445. Retrieved from the Internet on Mar. 28, 2016 at <URL: http://jcm.asm.org>.

Gouma, et al., TiO2-based Gas Sensors as Thick or Thin Films: An Evaluation of the Microstructure. Proceedings of the International Symposium on Dielectric Ceramics, May 2-6, 1998 and Ceramic Transactions: Dielectric Ceramic Materials, (1999) vol. 100, pp. 419-428, The American Ceramic Society, Westerville, Ohio.

\* cited by examiner

Electrochemical polymerization process of PANI prior to doping

Schematic of a block diagram of a universal readout system with a sensor.

HYDROGEN BREATH ANALYZER AND BREATH TEST METHOD

RELATED APPLICATIONS

This application is a U.S. National Phase Patent Application of International Patent Application No. PCT/US2019/065544, filed Dec. 10, 2019, which claims priority to U.S. Provisional Application No. 62/777,752, filed Dec. 10, 2018. The entirety of each of these applications is incorporated herein by reference.

FIELD OF THE INVENTION

The present application relates generally to a breath analyzer and breath test method for detecting hydrogen gas in the range of 1-100 ppm in a human breath sample to determine the presence of a gastrointestinal disorder in a subject's digestive tract.

BACKGROUND OF THE INVENTION

Various types of hydrogen microsensors are known. Such microsensors can use different mechanisms to detect hydrogen gas. Palladium is used in many of these sensors, as palladium selectively absorbs hydrogen gas and forms the compound palladium hydride. Thick-film hydrogen sensor designs rely on the fact that palladium metal hydride's electrical resistance is greater than the palladium's resistance. In these systems, the absorption of hydrogen is accompanied by a measurable increase in electrical resistance. However, palladium-based sensors have a strong temperature dependence, which makes their response time too large for gas flow detection. Palladium sensors also need to be protected against compounds present in human breath samples, such as carbon monoxide, sulfur dioxide, and hydrogen sulfide.

Ion Mobility Spectrometry (IMS) is a known analytical technique that uses ultraviolet ionization to separate and identify molecules in the gas phase based on their mobility in a carrier buffer gas. The mobility of molecules varies based on the size of the molecules, which can range from a few millimeters to several meters, depending on the specific application. IMS was developed to detect trace amounts of gases in the air and is generally used to detect harmful substances in low concentrations, including at workplaces and in the environment. IMS instruments are extremely sensitive stand-alone devices and can measure gases in low concentrations (e.g., parts per billion and/or parts per million), but are often coupled with mass spectrometry, gas chromatography, or high-performance liquid chromatography to achieve a multi-dimensional separation. The measurement time usually required for IMS instruments is between 10 and 60 minutes.

Reversible and irreversible chemochromic hydrogen sensors are also known. Chemochromic hydrogen sensors include a smart pigment paint that visually identifies hydrogen leaks by a change in color. A flexible substrate can be used with pigment paint for the application of detecting tape. The measurable color change is usually exposed in conditions having greater than 1% hydrogen.

Electrically-conductive polymers, such as polyaniline, polypyrrole, and polythiophene, have also been used to develop chemical sensors. Electrically-conductive polymers are highly desirable because they are inexpensive and easy to synthesize. Of the conducting polymer sensors, polyaniline appears to be the most widely studied due to its ease of synthesis and stability in air. It has also been shown that a field effect transistor having two layers, including palladium and polyaniline, can be used to detect hydrogen. These sensors operate at 90° C. and display fast response times. There has also been recent evidence that electrically-conducting polymers may have some ability to store hydrogen. However, one of the shortcomings of gas sensors using electrically-conductive polymers includes selectivity towards a particular gas in various coexisting gases.

It would be advantageous to provide a hydrogen gas sensor that is not subject to the response limitations of conventional polyaniline. It would also be advantageous to provide a hydrogen gas sensor that is able to operate at room temperature. Still further, it would be desirable to provide a breath analyzer that controls humidity levels within an optimal range and that has a hydrogen gas sensor comprising a blended electrically-conductive polymer.

SUMMARY OF THE INVENTION

In some embodiments, the present disclosure provides a handheld, portable breath analyzer including a main body and a removable mouthpiece. The removable mouthpiece removably attaches to the main body. The main body includes a sensor, a processor, a power source, and an electrical circuit. The electrical circuit operably connects the power source to the sensor and connects the sensor to the processor. The sensor includes a conductive material and a hydrogen selective material in contact with the conductive material. The hydrogen selective material has a resistivity that increases in response to increased concentration of hydrogen and has a resistivity that increases in response to a predetermined range of humidity. Humidity surrounding the sensor is controlled within the predetermined range of humidity. The hydrogen selective material includes polyaniline, and the polyaniline is doped with a dopant that increases pH sensitivity of the polyaniline. The polyaniline has a resistivity that increases in response to increased concentration of hydrogen. The processor detects resistivity of the sensor and uses the resistivity to calculate a concentration of hydrogen.

In other embodiments, the present disclosure provides a handheld, portable breathalyzer, including a sensor, an analog front-end circuit, a microcontroller, a display, and a memory. The display, the memory, and the analog front-end circuit are each electrically connected to the microcontroller. The sensor includes a conductive material and a hydrogen selective material in contact with the conductive material. The hydrogen selective material has a resistivity that increases in response to increased concentration of hydrogen, and also has a resistivity that increases in response to a predetermined range of humidity. Humidity surrounding the sensor is controlled within the predetermined range of humidity. The hydrogen selective material includes polyaniline, and the polyaniline is doped with a dopant that increases pH sensitivity of the polyaniline. The polyaniline has a resistivity that increases in response to increased concentration of hydrogen.

Certain other embodiments provide a breath test method for screening for a gastrointestinal disorder. The method includes the steps of providing a portable, hand-held breath analyzer that includes a main body and a removable mouthpiece. The removable mouthpiece removably attaches to the main body. The main body includes a sensor, a processor, a power source, and an electrical circuit. The electrical circuit operably connects the power source to the sensor and connects the sensor to the processor. The sensor includes a conductive material and a hydrogen selective material in contact with the conductive material. The hydrogen selective material has a resistivity that increases in response to increased concentration of hydrogen. The method further includes controlling humidity in an environment surrounding the sensor such that the humidity is within a predetermined range. The method also includes prompting a subject to exhale a breath sample into the removable mouthpiece, and allowing the processor to measure a resistivity of the sensor that occurs when the breath sample contacts the sensor. The method can further include designating the subject as having an increased likelihood of having a gastrointestinal disorder if the measured resistivity is above and/or beneath a predetermined value.

Still other embodiments provide a breath test method for diagnosing a gastrointestinal disorder. The method includes the step of providing a portable, hand-held breath analyzer that includes a main body and a removable mouthpiece that removably attaches to the main body. The main body includes a sensor, a processor, a power source, and an electrical circuit. The electrical circuit operably connects the power source to the sensor and connects the sensor to the processor. The sensor includes a conductive material and a hydrogen selective material in contact with the conductive material. The hydrogen selective material has a resistivity that increases in response to increased concentration of hydrogen. The method further includes controlling humidity in an environment surrounding the sensor such that the humidity is within a predetermined range. The method also includes prompting a subject to exhale a breath sample into the removable mouthpiece and allowing the processor to measure a resistivity of the sensor that occurs when the breath sample contacts the sensor. Still further, the method includes diagnosing the subject as having a gastrointestinal disorder if the measured resistivity is above and/or beneath a predetermined value.

DETAILED DESCRIPTION OF PREFERRED EMBODIMENTS

Figure 1:
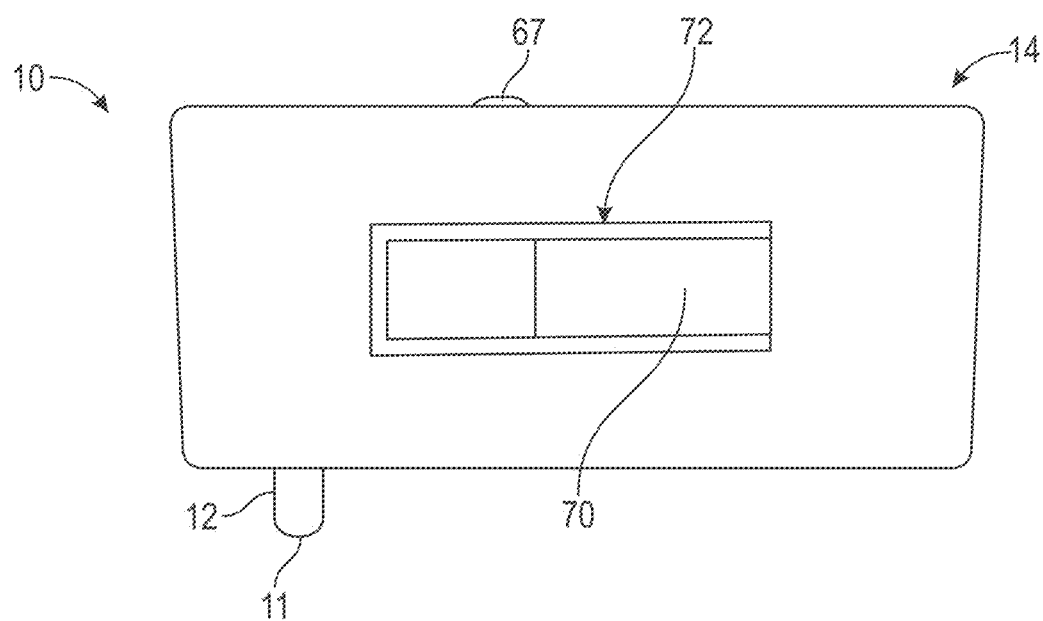
FIG. 1 is a top view of a breath analyzer in accordance with an embodiment of the present disclosure.

The following detailed description is to be read with reference to the drawings, in which like elements in different drawings have like reference numerals. The drawings, which are not necessarily to scale, depict selected embodiments and are not intended to limit the scope of the invention. Skilled artisans will recognize that the examples provided herein have many useful alternatives that fall within the scope of the invention.

The present disclosure provides an improved breath analyzer and breath test method to detect hydrogen gas in a human breath sample to detect the presence of a gastrointestinal disorder (e.g., celiac disease, non-celiac gluten sensitivity, lactose intolerance, fructose intolerance, or small bowel bacterial overgrowth) in the subject's digestive tract. The improved breath analyzer and breath test are more diagnostically accurate than existing devices and methods.

Figure 2:
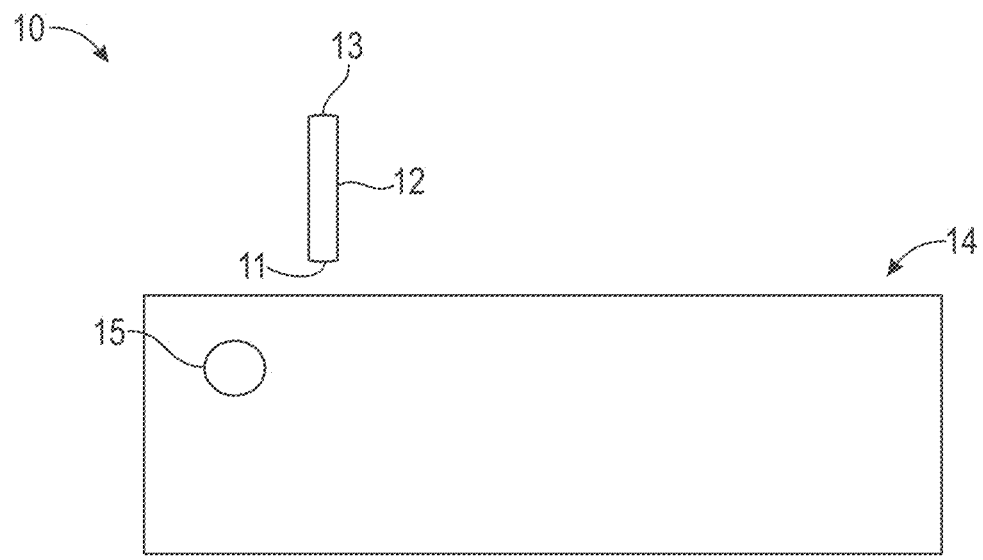
FIG. 2 is a side view of the breath analyzer of FIG. 1, showing the mouthpiece removed from the main body of the breath analyzer.

Referring to the drawings, and in particular, FIGS. 1 and 2, there is shown a breath analyzer of the present disclosure generally represented by reference numeral 10. The breath analyzer 10 includes a mouthpiece 12. The mouthpiece 12 has two open ends, including a first end 11 and a second end 13. In more detail, a subject exhales a breath sample into the first end 11 of the mouthpiece 12, which then travels through the mouthpiece 12 and exits through the second end 13 of the mouthpiece 12. The mouthpiece 12 can comprise any suitable type of material, including, but not limited to, plastic or metal.

The breath analyzer 10 also includes a main body 14 attached to the mouthpiece 12. The main body 14 can comprise plastic, metal, or any other suitable material. In some cases, the main body 14 and the mouthpiece 12 comprise the same material. In other cases, the main body 14 and the mouthpiece 12 comprise different materials. The main body 14 can have any desired size and shape. However, in most embodiments, the breath analyzer 10 is intended to be portable and thus will be of a sufficiently small size to allow its portability.

The mouthpiece 12 can be integral with the main body 14, or can be a separate structure that is connected to the main body 14. In instances where the mouthpiece 12 is a separate structure connected to the main body 14, the mouthpiece 12 can be placed inside the main body 14 through a hole 15 in the main body 14, using e.g., a push-in, screw-in, or tack-in motion.

In one embodiment, the mouthpiece 12 is permanently attached to the main body 14. In such instances, the mouthpiece 12 can be securely mounted on the main body 14, extending straight out from the main body 14 or at an angle from the main body 14. These alternate configurations allow the eyes of the subject taking the breath sample to either directly face the main body or to face away from main body 14 while taking the breath sample. The mouthpiece 12 can be permanently mounted to an opening in the main body 14 using a receptacle made of plastic or metal or any other material. In other cases, the mouthpiece 12 can be permanently attached to the main body 14 without the use of a receptacle.

FIGS. 1 and 2 illustrate an exemplary embodiment of the breath analyzer 10. FIG. 1 shows the breath analyzer 10 with the mouthpiece 12 attached to the main body 14, whereas FIG. 2 shows the breath analyzer 10 with the mouthpiece 12 detached from the main body 14. In some cases, the mouthpiece 12 is a single use mouthpiece that is disposed of after use, and that can be replaced with a new mouthpiece for each new user.

The mouthpiece 12 can be attached to an exterior of the main body 14 or can extend into the main body 14 of the breath analyzer 10. The mouthpiece 12 can be attached anywhere on or within the breath analyzer 10, provided that a first end 11 of the mouthpiece 12 projects out of the main body 14. The mouthpiece 12 can attach to the breath analyzer 10 via any suitable type of connection, including a straight connection, push-in connection, or screw-in connection, or have another type of connection within the main body 14 of the breath analyzer 10. In some cases, the mouthpiece 12 can be glued or can use any other type of adhesive to adhere the mouthpiece 12 to the main body 14.

The mouthpiece 12 can have any desired shape. For example, the mouthpiece 12 can be oblong, cylindrical, cone-shaped, or straw-shaped. The shape of the mouthpiece 12 should be such that the lips of the subject are able to wrap around the mouthpiece 12 in a tight manner. The mouthpiece 12 can optionally include a self-sealing, one-way valve to seal the breath sample from the surrounding air once the breath sample exits the mouthpiece 12 and enters the main body 14 of the breath analyzer 10.

Figure 6:
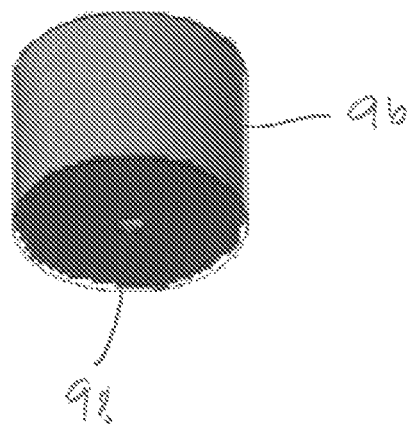
FIG. 6 is a perspective view of a filter case of an embodiment of the present disclosure.

Optionally, the main body 14 can include a lower section 22 (FIG. 3) and an upper section 24 (FIG. 6). The upper section 24 is positionable on top of the lower section 22. The upper section 24 can be removably attached to the lower section 22 in any conventional manner, including a mechanical connection (e.g., screws) or an adhesive (e.g., glue). In preferred embodiments, the upper section 24 is positionable on top of the lower section 22 such that a bottom perimeter edge 23 of the upper section 24 aligns with an upper perimeter edge 25 of the lower section 22.

Figure 3:
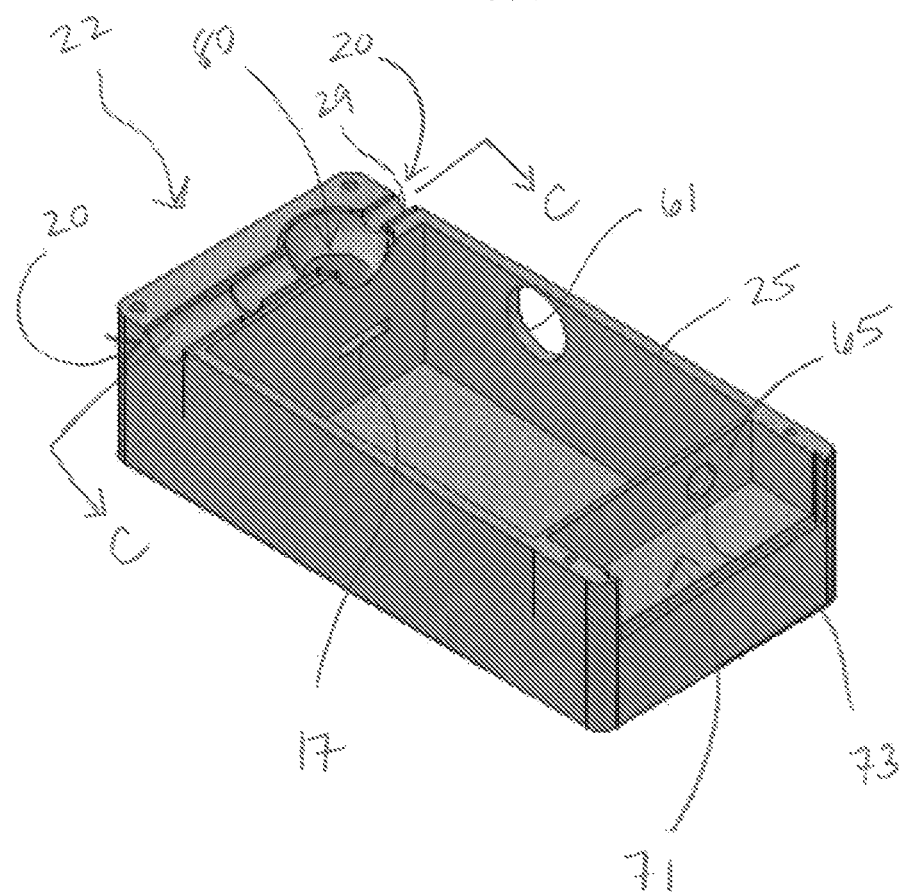
FIG. 3 is a perspective view of a lower section of the main body of an embodiment of a breath analyzer of the present disclosure.
Figure 5:
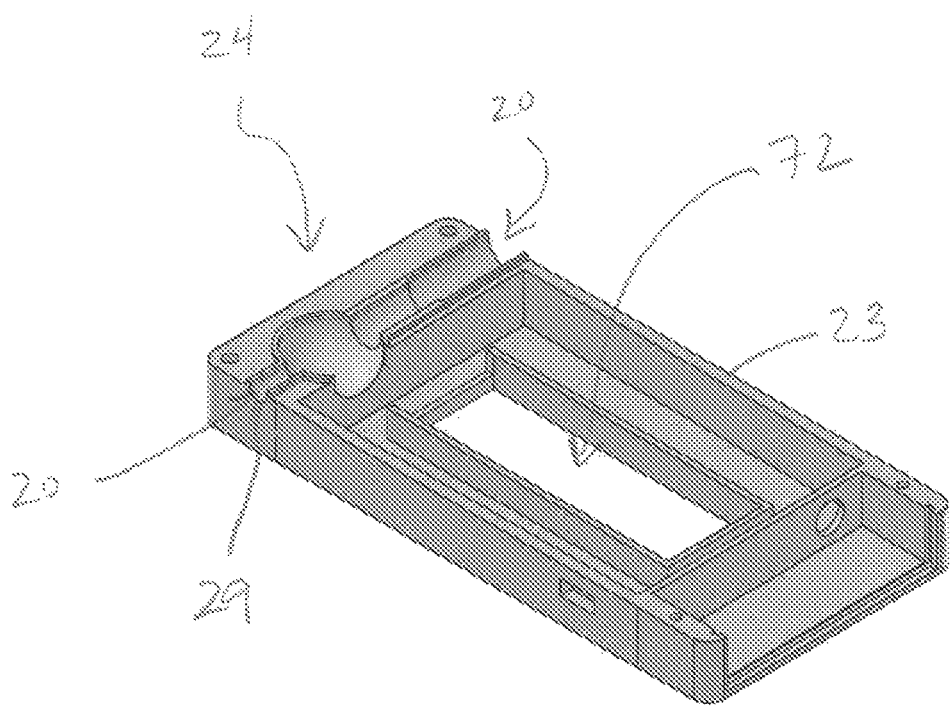
FIG. 5 is a perspective view of a top section of an embodiment of a breath analyzer of the present disclosure.

As shown in FIGS. 3 and 5, an elongated channel 20 can be formed in the main body 14. The channel 20 extends from at least one side of the main body 14 inwardly toward another side of the main body 14. The channel 20 can extend either entirely or partially between opposite sides of the main body 14. FIGS. 3 and 5 show an embodiment where the channel 20 extends entirely between opposite sides of the main body 14. The channel 20 is configured to receive the second end 13 of the mouthpiece 12. Thus, the breath sample is exhaled into the first end 13 of the mouthpiece 12 and travels through the second of the mouthpiece 12 and then out into the channel 20.

The breath analyzer 10 also includes a gas sensor 50. The gas sensor 50 is positioned within the main body 14 and is configured to detect hydrogen gas that comes into contact with the gas sensor 50. In particular, the gas sensor 50 is capable of detecting hydrogen gas present in a human breath sample when the breath sample exits the mouthpiece 12 and contacts the gas sensor 50.

Figure 4:
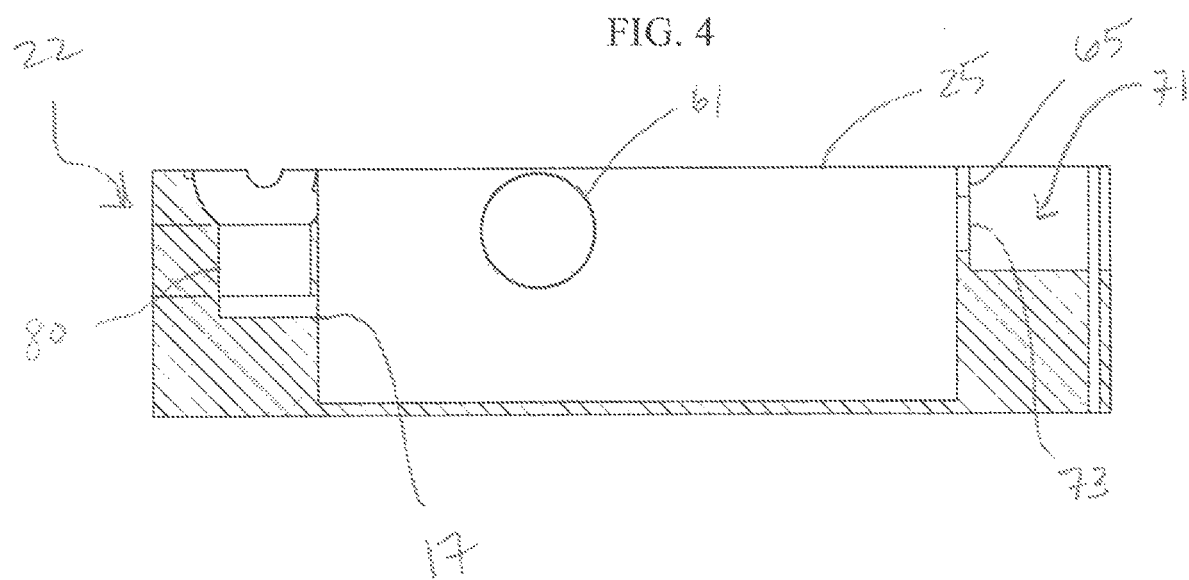
FIG. 4 is a cross-sectional view of the breath analyzer taken along line C-C of FIG. 3.

In preferred embodiments, the gas sensor 50 is positionable in a chamber 80 formed in the main body 14. Where the main body 14 includes an upper section 22 and a lower section 24, the chamber 80 can be positioned in the lower section 24 of the main body 14. As shown in FIGS. 3 and 4, the chamber 80 can be formed as a recessed opening in the main body 14. The main body 14 can have a slot 17 formed therein, particularly near a bottom end of the chamber 80. This allows the gas sensor 50 to be slidably received in the bottom end of the chamber 80 via the slot 17. In some cases, the gas sensor 50 is slid into the chamber 80 through the slot 17, and attached to the chamber 80 using, but not limited to, glue, another type of adhesive, or conventional mechanical fasteners.

The chamber 80 is spaced from the side of the main body 14 where the mouthpiece 12 is attached. The gas sensor 50 is also spaced from the second end 13 of the mouthpiece 12 such that the breath sample must travel out of the mouthpiece 12, through the channel 20, and into the chamber 80. This arrangement is advantageous as it allows the breath sample to travel through the main body 14 and toward the gas sensor 50 by passive diffusion, as opposed to conventional methods. Passive diffusion of the breath sample enables the gas sensor 50 to more accurately and efficiently measure the hydrogen gas concentration present in the breath sample as compared to conventional methods. The above-described structural arrangement of the present breath analyzer 10 (particularly the relative positioning of the gas sensor 50 relative to the mouthpiece 12) ensures that the breath sample contacts the gas sensor 50 at a much slower rate than with conventional gas sensors.

When the subject exhales into the mouthpiece 12, the breath sample (e.g., either some of the breath sample or all of the breath sample) will come into contact with the gas sensor 50. The portion of the breath sample that does not contact the gas sensor 50 will diffuse toward an end 29 of the channel 20 that is distal to the mouthpiece 12, where that portion of the breath sample will exit the main body 14.

The breath analyzer 10 further can also include a humidity control device. In some embodiments, the humidity control device comprises a desiccant. The desiccant is positioned adjacent to the gas sensor 50 such that a breath sample travels through the desiccant prior to coming into contact with the gas sensor 50. In this manner, the desiccant is able to control (e.g., decrease) the amount of humidity that contacts the gas sensor 50. This particular arrangement is advantageous, as the gas sensor 50 will become less sensitive to detecting hydrogen gas as humidity levels increase. Ideally the desiccant is capable of removing water from the gas stream (e.g., the breath sample) and has no affinity to analytic gas.

In certain embodiments, the desiccant comprises aluminosilicates. However, it is contemplated that other materials can alternatively be used as the desiccant. Where the desiccant comprises aluminosilicates, the desiccant is also able to block ammonia gas from reaching the gas sensor 50. In some instances, the desiccant is provided in the form of crystals (e.g., aluminosilicate crystals). In such cases, the desiccant can be positioned between two substrates to help hold the crystals together. Preferably, the substrates each comprise one or more layers of mesh. The substrates (e.g., mesh) can each comprise (consist of, or consist essentially of) copper or another metal. The substrates can be the same material as each other or can comprise a different material from each other.

Figure 40:
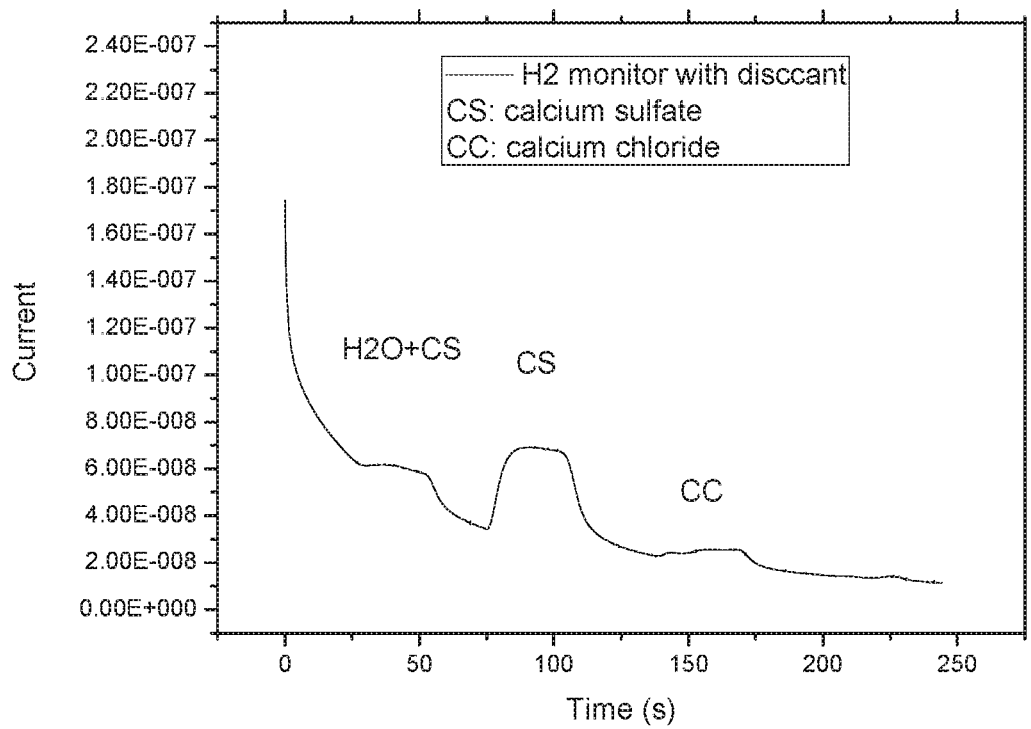
FIG. 40 shows the results of an $H_2$ adsorption test using calcium oxide and calcium sulfate as a desiccant.
Figure 41:
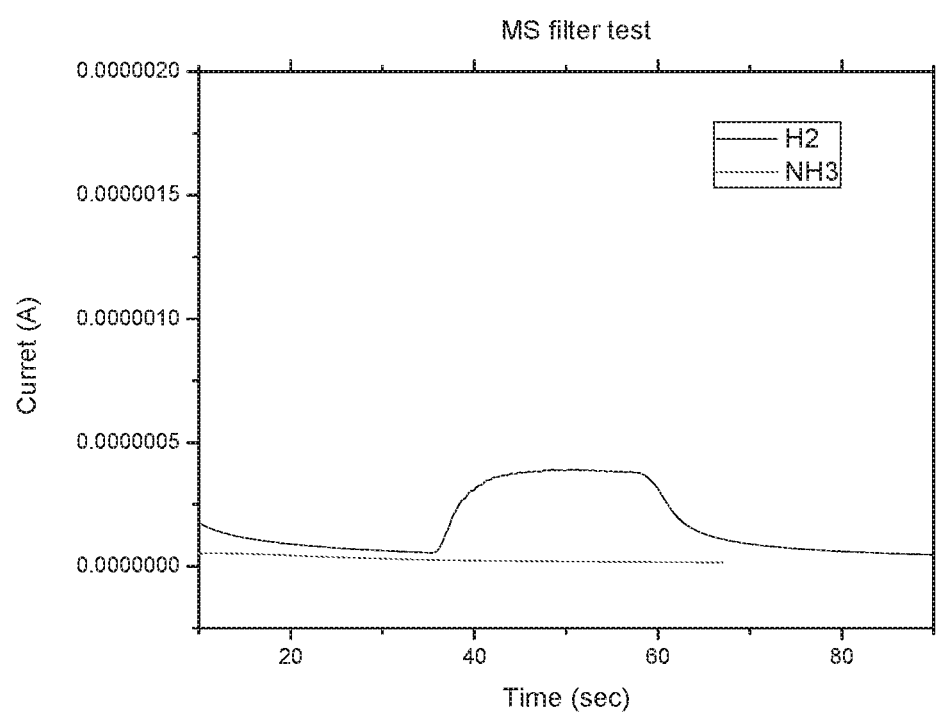
FIG. 41 shows the results of an $H_2$ and $NH_3$ gas adsorption test on a molecular sieve (MS) filter.

Calcium Chloride (CC), Calcium Sulfate (CS), and Molecular Sieve (MS) were tested as desiccants to optimize the performance of the $H_2$ sensor of the present disclosure. The desiccant was placed in front of the gas sensor, and then a known concentration of $H_2$ gas stream was flowed through the desiccant and the gas sensor 50 for detection. These results are in FIG. 40, which shows that calcium chloride retains most of the $H_2$ gas and implies the deterioration of sensitivity of the gas sensor. Both calcium chloride and calcium sulfate can remove water content completely, suggesting that the sensor measurement can be taken in dry conditions. A molecular sieve (MS) desiccant can remove 10-20% water content and also shows low adsorption of Hz, as shown in FIG. 41. Any molecular sieve can be used as a desiccant in the present breath analyzer 10 and related method. In addition, $NH_3$ can be completely removed by the molecular sieve desiccant, which may suggest the reduction of $NH_3$ effect on the gas sensor 50 of the present disclosure.

As shown in FIG. 6, the breath analyzer 10 can also include a case 96. The case 96 is configured to receive (i.e., hold) the desiccant or other filter. In embodiments that also include the substrates, both the substrates and the desiccant are positionable within the case 96. The case 96 is positionable in the main body 14. In preferred embodiments, the case 96 is positioned in the chamber 80 above the gas sensor 50. The case 96 has two holes 98 positioned therein (e.g., one on a top surface of the case 96 and another on a bottom surface of the case 96). Although only one hole 98 is shown in the drawings, it should be understood that the opposite side of the case 96 has a similar hole therein to allow the breath In some embodiments, the breath analyzer 10 includes a hygrometer. The hygrometer will measure the humidity level in the breath sample and provide a humidity reading. A preferred range of relative humidity levels is from 0.1% to 15% for the particular gas sensor 50 used in the present disclosure, with the optimal humidity level of the gas sensor 50 being around 5%. Thus, the hygrometer will indicate whether the humidity levels are within such a desired range prior to taking any measurements with the gas sensor 50. In this manner, the breath analyzer 10 of the present disclosure ensures that sensor measurements are taken at optimal humidity levels. Where the hygrometer indicates that the humidity levels are below the desired range, an amount of the desiccant can be removed until the hygrometer indicates that the desired humidity levels have been obtained. Where the hygrometer indicates that the humidity levels are above the desired range, more of the desiccant can be added into the chamber 80 (particularly into the case 96 in embodiments where the case is present).

Figure 9:
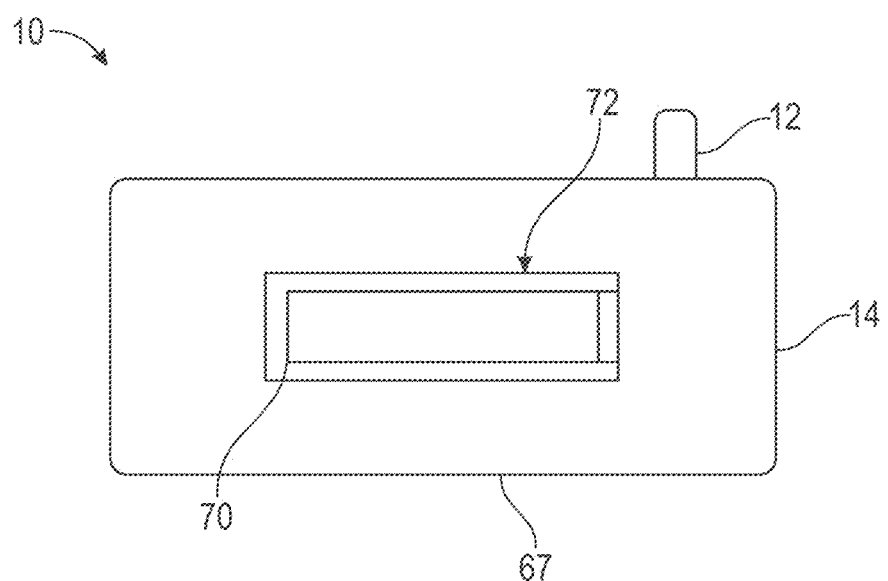
FIG. 9 is a top view of a breath analyzer of an embodiment of the present disclosure.
Figure 10:
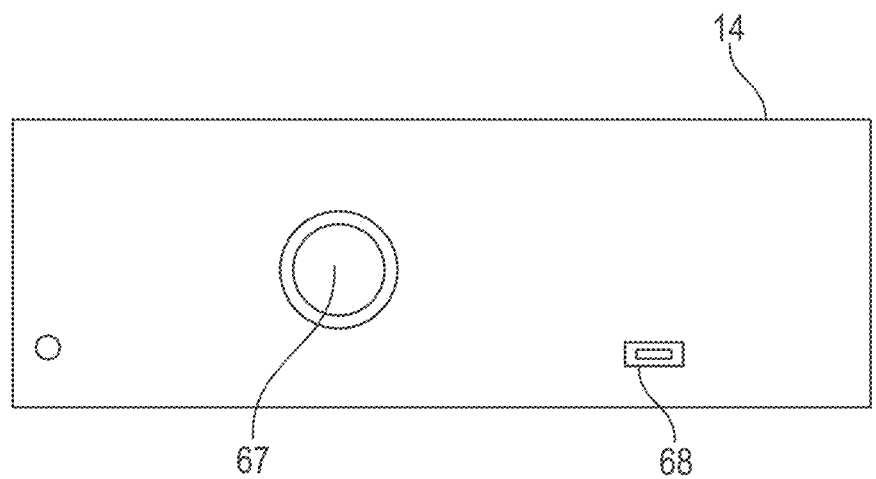
FIG. 10 is a side view of an embodiment of a breath analyzer of the present disclosure.
Figure 11:
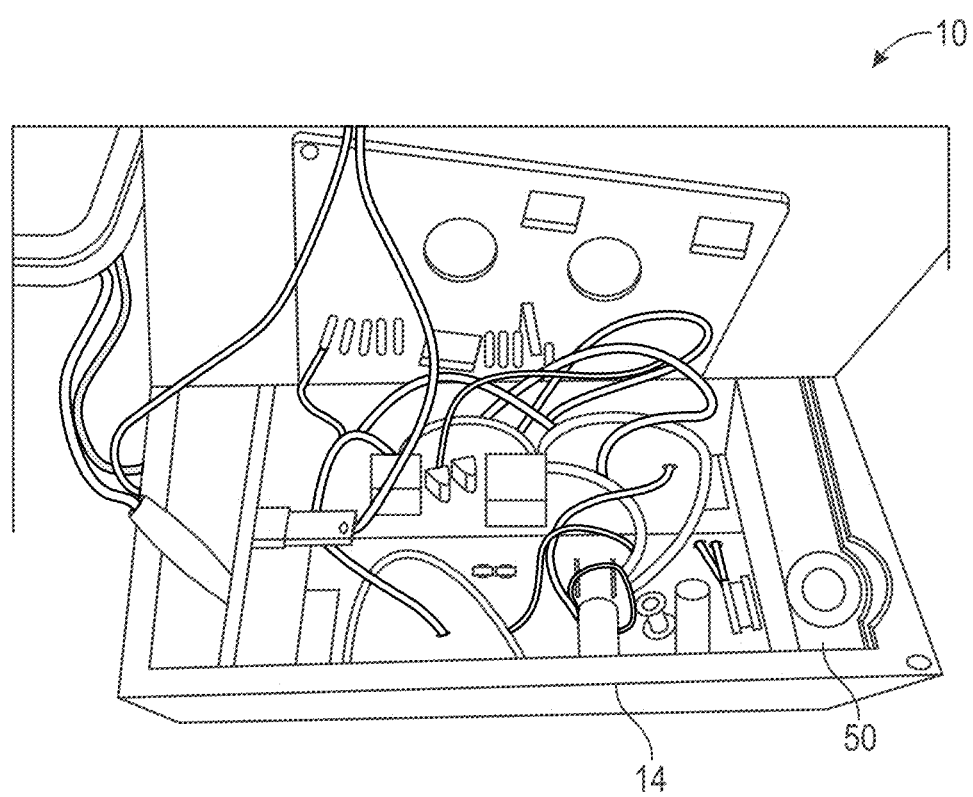
FIG. 11 is a view of an interior of an embodiment of a breath analyzer of the present disclosure.

In some embodiments, the breathalyzer 10 includes a display 70 and a processor 64. The display 70 is electrically connected to the processor 64. In some cases, the display 70 is configured to visually display the concentration of hydrogen gas detected by the gas sensor 50. In other cases, the display 70 shows results of a comparison between concentrations of hydrogen gas between two or more different breath samples. In some embodiments, the display 70 is a window display provided in an opening 72 on the main body 14 of the breath analyzer 10 (see FIGS. 1, 5, and 9). In an alternative embodiment, the results can be displayed, with the use of Bluetooth technology or any other wireless data transmitter, through a computer portal or other device that can be either stationary or portable.

Figure 12:
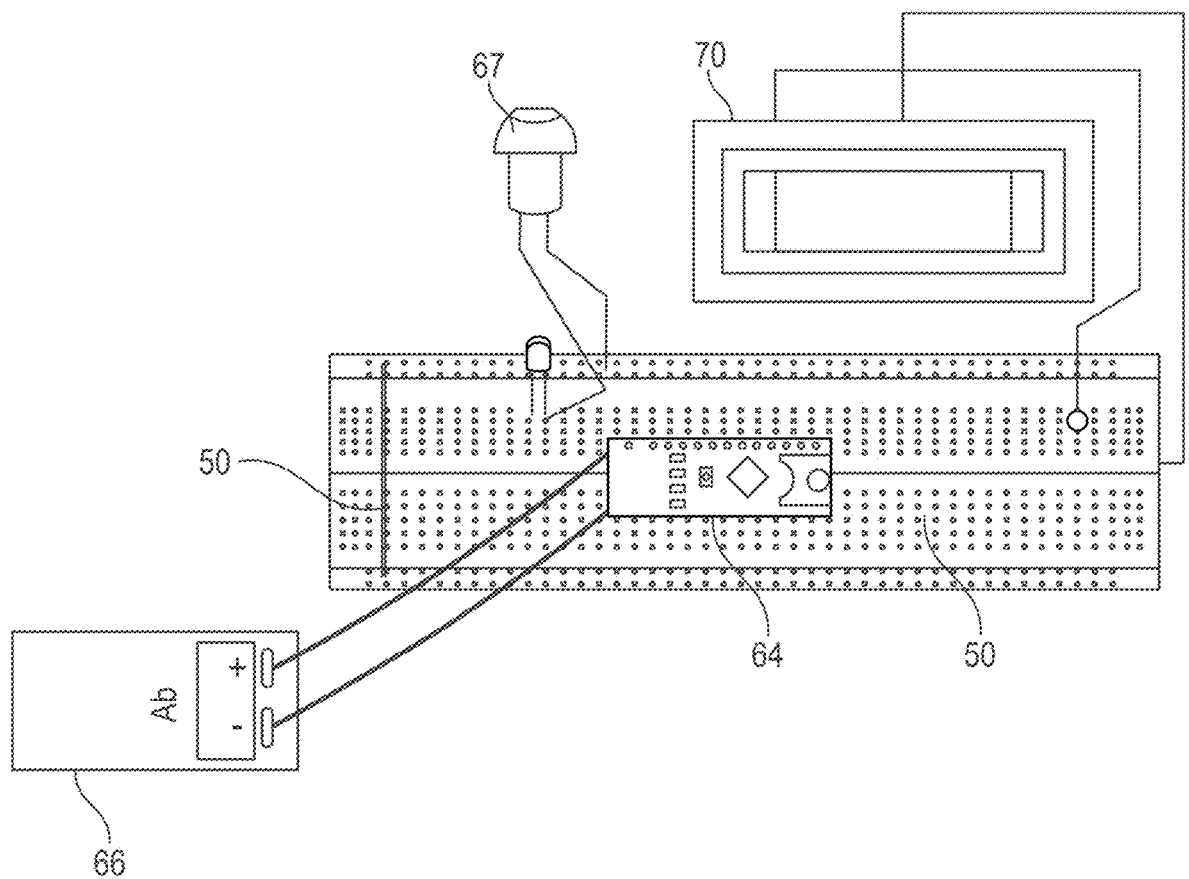
FIG. 12 is a schematic illustrating an electrical circuit of an embodiment of a breath analyzer of the present disclosure.
Figure 13:
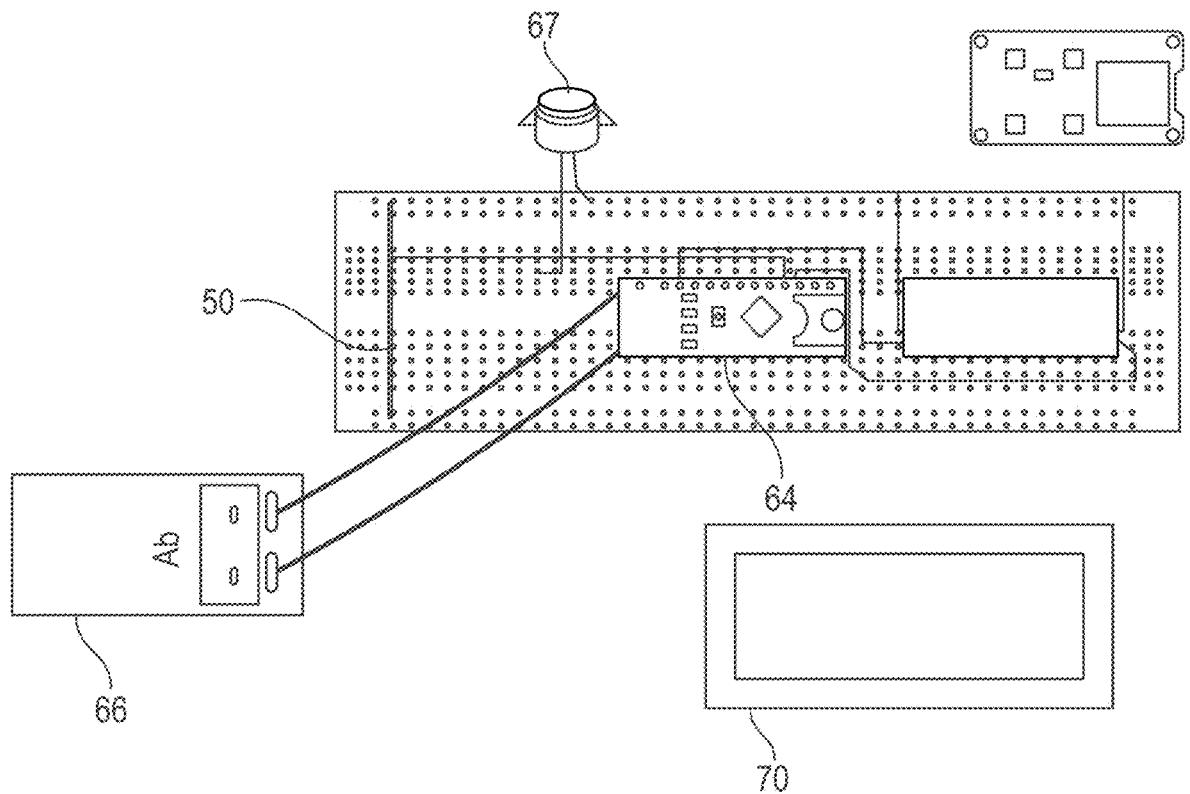
FIG. 13 is a schematic illustrating an electrical circuit of an embodiment of the breath analyzer of the present disclosure.
Figure 14:
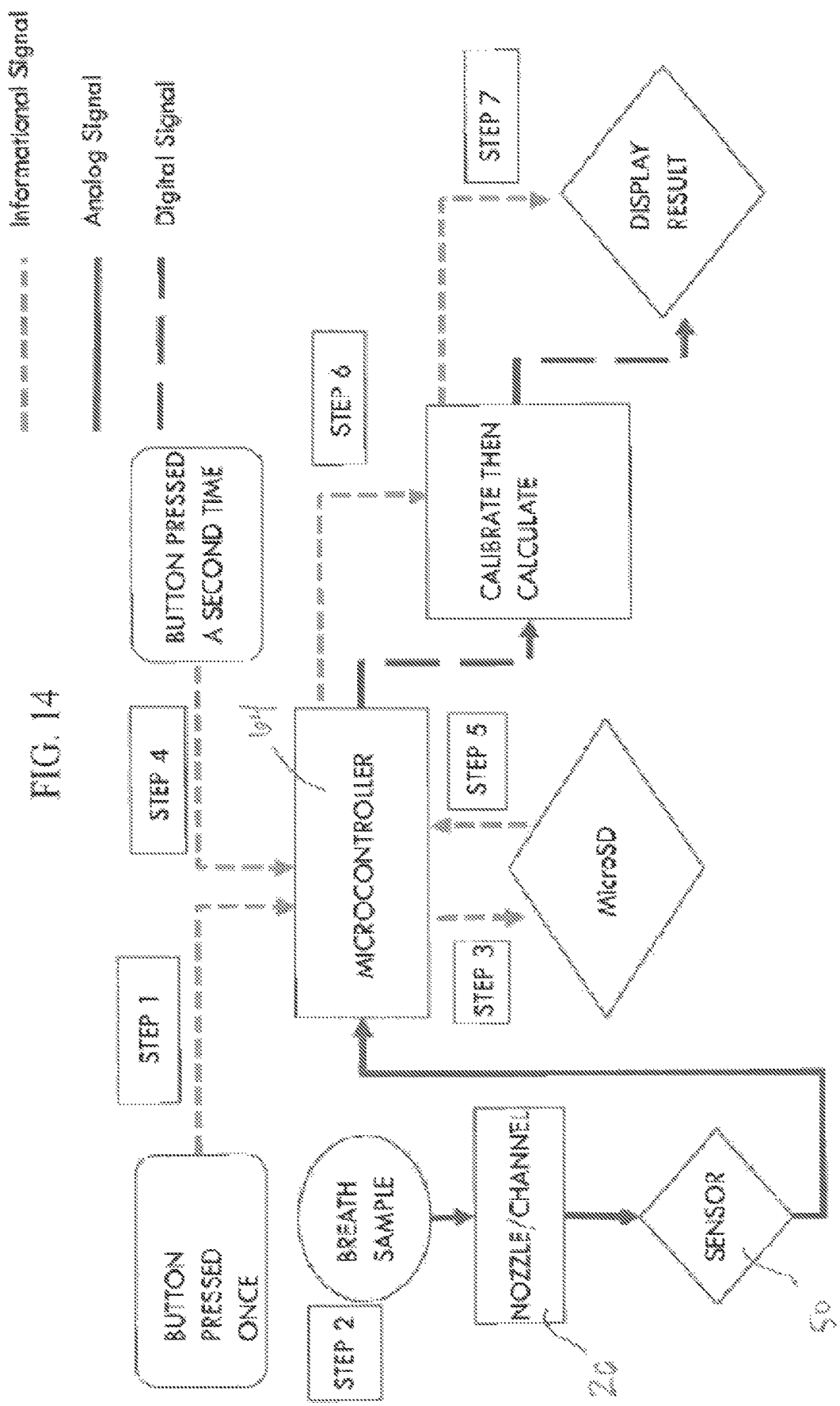
FIG. 14 is a flow diagram of a breath test method of the present disclosure.
Figure 15:
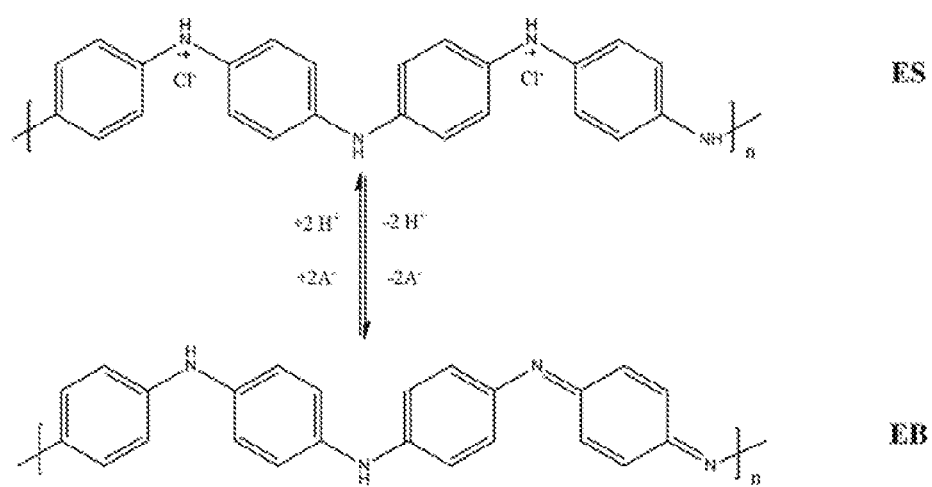
FIG. 15 shows an acid-base (emeraldine salt (ES)-emeraldine base (EB)) transition for polyaniline.

The main body 14 also includes a power source 66. FIGS. 12 and 13 are electrical schematics illustrating the electrical connection between various components of the breath analyzer 10 of the present disclosure. As shown, the gas sensor 50, processor 64, and power source 66 are electrically connected via the electrical circuit 60. The processor 64 can be any desired processor known in the art. In some cases, the processor 64 is a microcontroller. In certain cases, the processor 64 is an Arduino microcontroller.

Figure 8:
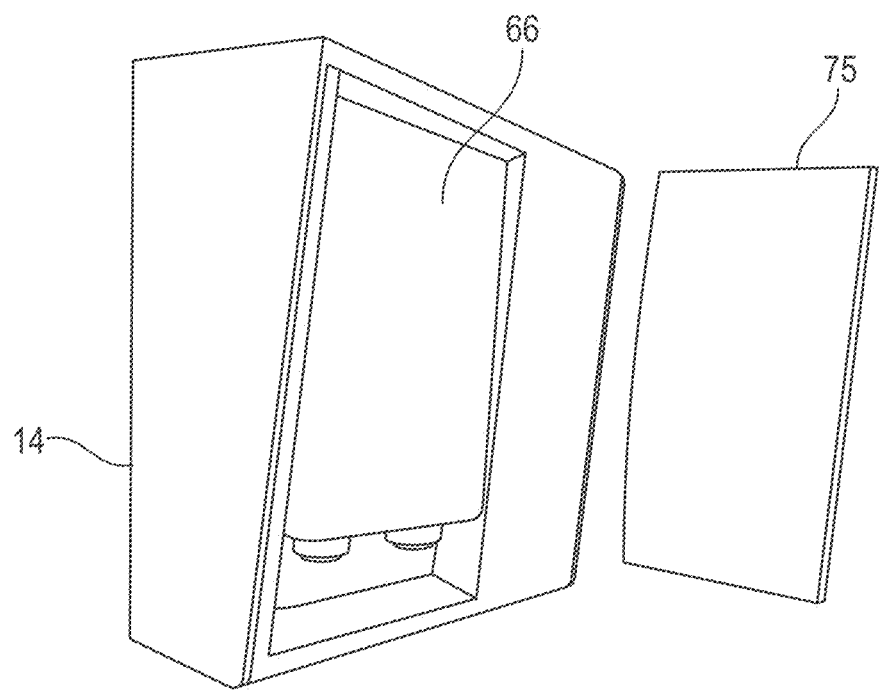
FIG. 8 is a perspective view of an embodiment of a breath analyzer of the present disclosure, showing a power source, as well as a closure detached from the main body of the breath analyzer.

The power source 66 can be a portable power source, such as a battery. The power source 66 is positionable in the main body 14. In some cases, the main body 14 has at least one interior vertical wall 65 defining a receptacle 71 for receiving the power source 66. The interior vertical wall 65 can have an opening 73 for receiving cables of the power source 66 therethrough. The breath analyzer 10 can also have a closure 75 attached to the main body 14. In some cases, the closure 75 is removably attached to the main body. The closure 75 can be positioned in a closed position to cover the power source 66, or in an open position (FIG. 8) to expose the power source 66.

The main body 14 also includes a press/release button 67 and an on/off switch 68. The on/off switch 68 allows the breath analyzer 10 to be turned on and off. When activated (e.g., pressed), the press/release button 67 electrically connects the gas sensor 50 to the electrical circuit 60. When deactivated (e.g., de-pressed), the press/release button 67 electrically disconnects the gas sensor 50 from the electrical circuit 60. The press/release button 67 is activated (e.g., pressed) when the subject using the breath analyzer 10 exhales, and is de-activated (e.g., de-pressed) when the subject using the breath analyzer 10 has finished exhaling. The press/release button 67 is coupled to the main body 14. In some cases, the press/release button 67 extends through a hole 61 in the main body 14.

The gas sensor 50 comprises an electrically-conductive polymer. In certain embodiments, the gas sensor 50 is polyaniline doped with camphorsulfonic acid. The gas sensor 50 can include thin-wire electrodes attached to the electrical circuit 60. When the gas sensor 50 detects hydrogen gas, the resistivity of the gas sensor 50 changes, providing an electrical signal to the electrical circuit 60 to generate current. The breath analyzer 10 is then able to convert the current to concentration of hydrogen gas.

A non-limiting example of materials for the gas sensor 50 is provided below.

Chemical reagents can be purchased from Sigma Aldrich or Thermo Fisher and used without further purification. Gases can be delivered by Airgas. The 3A form of crystalline metal aluminosilicates with a three-dimensional interconnecting network of silica and alumina tetrahedral from Sigma Aldrich can be used for removing $NH_3$ and $H_2O$ from the breath sample of the present disclosure. Prior to being used, particles can be placed in vacuum conditions with 150° C. heating. Thin-film interdigitated platinum film electrodes (IDA) (e.g., with a line spacing of 100 μm) on a substrate comprising silicon, Pyrex or highly polished alumina can be used, particularly of the type fabricated by the Electronic Design Center, Case Western University. On such silicon substrates, there can be provided 300 nm thick layer of thermally grown, electrically insulating silicon dioxide between the metallic interdigitated finger electrodes and the silicon substrate. A metal circuit can be deposited using physical vapor deposition (PVD) with a thickness of about 10-15 microns. The electrodes can be spaced by a range of from 1 μm to 100 μm using sputtering, electron-beam physical vapor deposition (EB-PVD) process, or cathodic arc deposition. Any of gold (Au), silver (Ag), platinum (Pt) or palladium (Pd) can be used as metal substrate materials for the gas sensor 50.

A non-limiting example of synthesizing and doping polyaniline for the gas sensor 50 is described below. This doped polyaniline can be used as the gas sensor 50 in any embodiment of the present disclosure.

Figure 16:
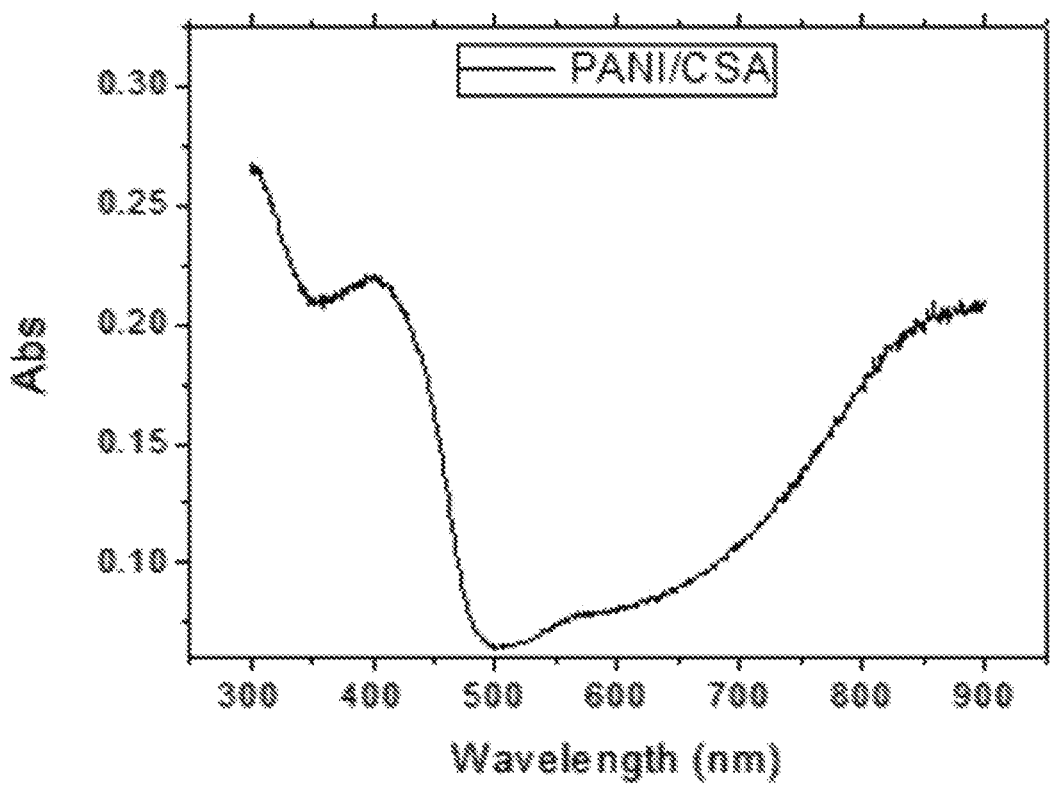
FIG. 16 is a graph showing the UV-vis spectra of secondary doped PANI/CSA.

Polyaniline (PANI) doped with HCl can be prepared by chemical oxidative polymerization of aniline in aqueous acidic medium (1M HCl) with ammonium persulfate (APS) as an oxidant. Higher polymerization yields can be obtained by using oxidant-to-monomer ratio of 1.2. Fifty ml of 0.48 M APS in 1M HCl can be added slowly to 50 ml of a 0.4M aniline solution in a beaker. The mixture was left to polymerize overnight at room temperature. The PANI precipitate was collected on a filter paper and washed repeatedly with 0.1M HCl followed by repeated washes with acetone. Deprotonation of the resulting PANI salt was performed by stirring the powder in an aqueous 0.1M $NH_4OH$ solution for 24 hours at room temperature, thus obtaining the emeraldine base (EB) form of polyaniline, which can then be washed with water repeatedly until neutral pH is obtained and then dried under vacuum for 48 hours at 60° C. A variety of acidic dopants can be secondary doped on polyaniline by optimizing the doping ratio and usage condition, including boronic acid, 4-dodecylbenzenesulfonic acid (DBSA), p-toluenesulfonic acid (TSA), sulfosalicylic acid (SSA), b-naphthalenesulfonic acid (NSA), Dinonylnaphthalenesulfonic acid (DNNSA), 4-hydroxybenzenesulfonic acid (HBSA), camphorsulfonic acid (CSA), and α, ω-alkanedisulfonic acid, $HO3S(CH2)nSO3H$ (n=1, 4, 6 and 12). Certain polymeric acid dopants can be used for hydrogen sensing, such as poly(methyl vinyl ether-alt-maleic acid) (PMVEA), poly(4-styrenesulfonic acid) (PSSA), and/or poly(acrylic acid) (PAA). Any (e.g., all) sensors of the present disclosure can comprise polyaniline doped with one or more of the materials recited in this paragraph. Where the gas sensor 50 is polyaniline doped with camphorsulfonic acid, polyaniline can be secondary doped with camphorsulfonic acid at a molar ratio of 1:2. A 0.5 wt % solution of the resulting PANI/CSA complex (37.5 mg PANI, 48 mg CSA) in 5 ml chloroform can be prepared and allowed to dissolve for 2 days with constant stirring. The solutions can be filtered with a 0.2 μm polytetrafluorethylene (PTFE) syringe filter to remove any particulate impurities. PANI doped with CSA can be confirmed by a UV-vis spectrum, as shown in FIG. 16.

Non-limiting examples of fabrication of the gas sensor 50 are provided below. The gas sensor 50 can be fabricated by the method described below in any embodiment of the present disclosure.

Figure 17:
FIG. 17 is an SEM image of a PANI/CSA film drop-casted from $CHCl_3$ solution.

A gas sensor 50 comprising a polyaniline (PANI) film sensor can be prepared using sophisticated methods for polymer film preparation, including drop casting, mechanical molding, chemical and physical deposition, or electrochemical polymerization. A PANI/CSA film, for example, can be prepared using drop-casting. Polyaniline solutions can be made by dissolving polyaniline in chloroform (e.g., 1.5 mg/mL), which is then drop-casted onto a surface of finger electrodes to prepare a film having a thickness of 100-200 microns. Drying and annealing can be performed under temperature conditions ranging from 60-120° C. (e.g., in a 70° C. oven), followed by washing with a washing solution (e.g., ethanol, methanol, water, or acetone) to remove excessive dopants. FIG. 17 shows the morphological structure of a PANI/CSA film in scanning electron micrograph (SEM) images.

Figure 31:
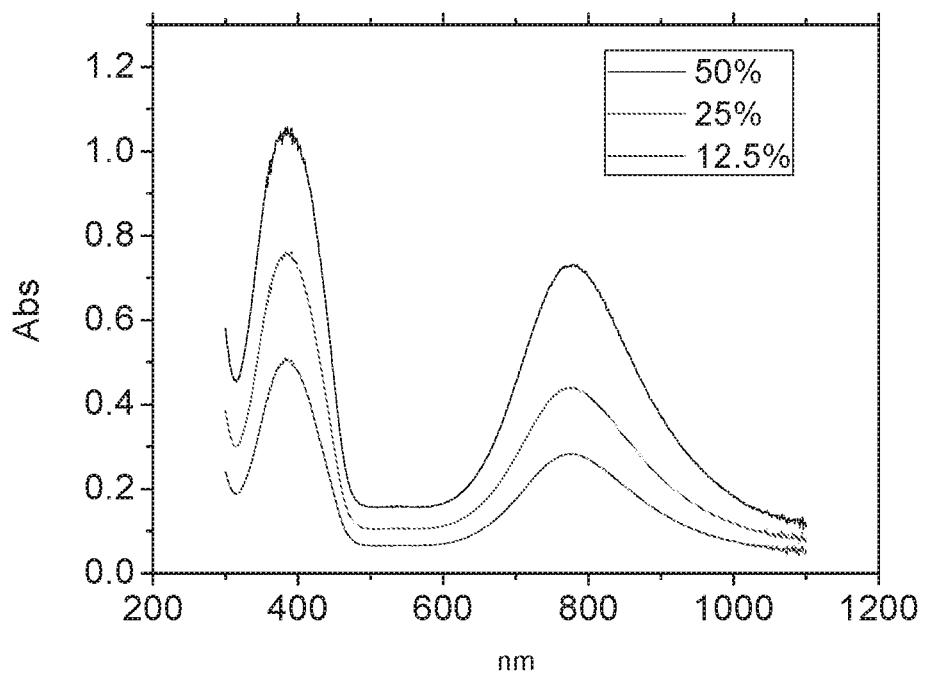
FIG. 31 shows results of comparison of the breath analyzer of the present disclosure to standard PANI.
Figure 32:
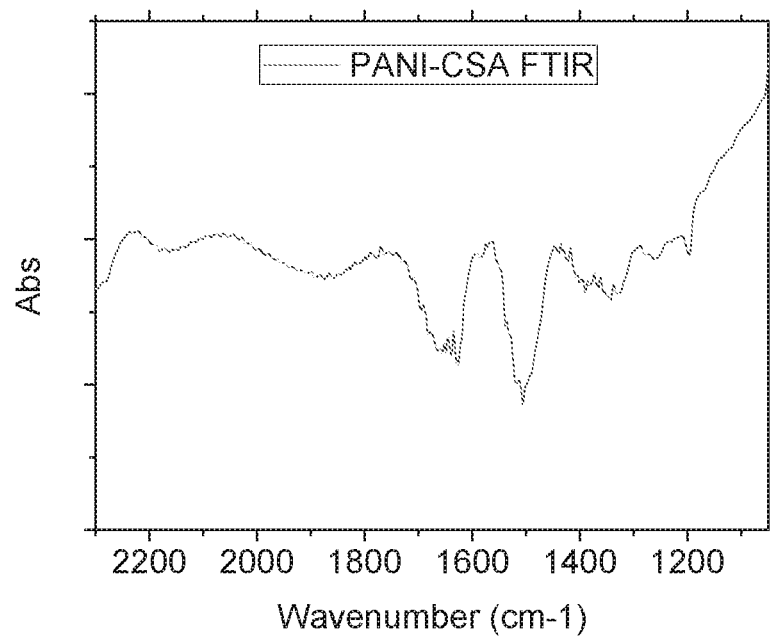
FIG. 32 shows Fourier transform infrared spectroscopy (FTIR) data that confirms the structure of ES-PANI.

Polymerized PANI can be characterized by (i) UV-vis (measuring concentration) (ii) FT-IR (characterizing functional group); or (iii) SEM—(studying morphology of the nanostructure). The UV-vis of polymerized PANI of the present disclosure is shown in FIG. 31, which shows the benzene feature absorption of 390 nm and conjugating with CSA for boarded peak around 800 nm. The PANI concentration is calibrated by a standard known PANI solution for determination of synthesized PANI. The chemical structure of PANI is confirmed by FT-IR in FIG. 32, which shows a wavelength feature of 1580 cm$^{-1}$ for C=C and a wavelength of 1300 cm$^{-1}$ for C—N bond. Spectral data are matched with a reference and can confirm the PANI polymerization results. The PANI-CSA can be doped in N-Methyl-2-pyrrolidone (NMP) and then used to cast onto gold and platinum finger electrodes for fabrication of the gas sensor 50. The electrodes can be provided by Electronic Design Center, Case Western Reserve University. This electrode consists of thick film printed interdigitated platinum, gold or silver lines on a 1 mm thick wafer substrate. Line width and gap is 0.1 mm. The overall dimensions of the wafer are 8 mm×8 mm. Prior to use, the electrodes can be cleaned by Piranhas solution for gold and methanol for platinum electrodes, and PANI films can be spun cast onto the electrode by adding 10 µL solution at 100 rpm. The thickness can be measured by ellipsometry within 400 nm to 800 nm. The results for both metals (i.e., gold and platinum) are listed in Table 3 below. The results of Table 3 indicate the similar thicknesses for both metals, with the coating being smoother on the gold electrode than on the platinum electrode.

TABLE 3

Thickness and roughness measurement based on ellipsometry

|  | Gold electrode | Pt Electrode |
|---|---|---|
| Cleaning | 1:1 Sulfuric acid and hydro peroxide | MeOH sonicate and rinse |
| Coating thickness | 1-3 micron | 1-3 micron |
| Conductivity in air | 1E-12 A/micron | 1.2E-12 A/micron |

Resistivity Measurement

Model 660D potentiostat analyzer from CH Instrument (Austin, TX) was used for taking the amperometric i-t measurements which were performed by applying a fixed potential of 0.1V to the gas sensor 50 and collecting the resulting current which changed as a function of gas passed over the surface of the gas sensor 50 at a fixed temperature (e.g., 25° C.). For this purpose, temperature can be in the range from 0° C. to 120° C. The resistivity (ρ) of the gas sensor 50 is calculated based on Equation 1, provided below, where L represents the gap between the electrode wires; A represents the cross-sectional area of current flow, and R represents voltage divided by current:

$$\rho = R \times A/L \qquad \text{Equation (1):}$$

Figure 33:
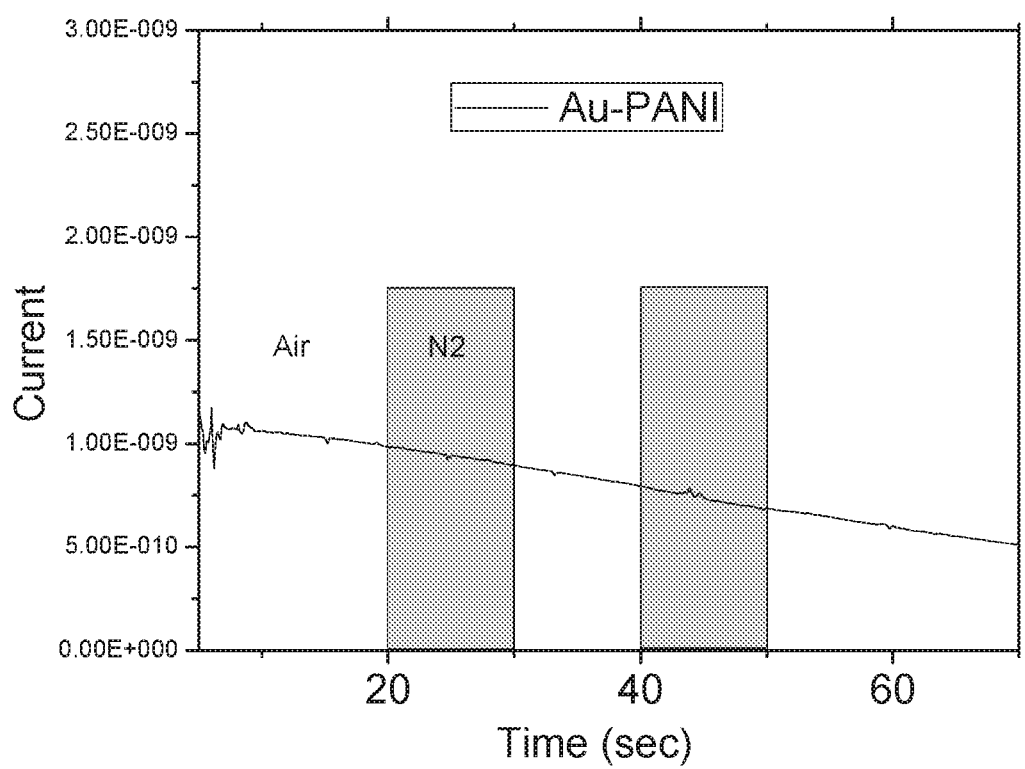
FIG. 33 shows the results of air control measurement and PANI-CSA on a gold finger electrode.
Figure 34:
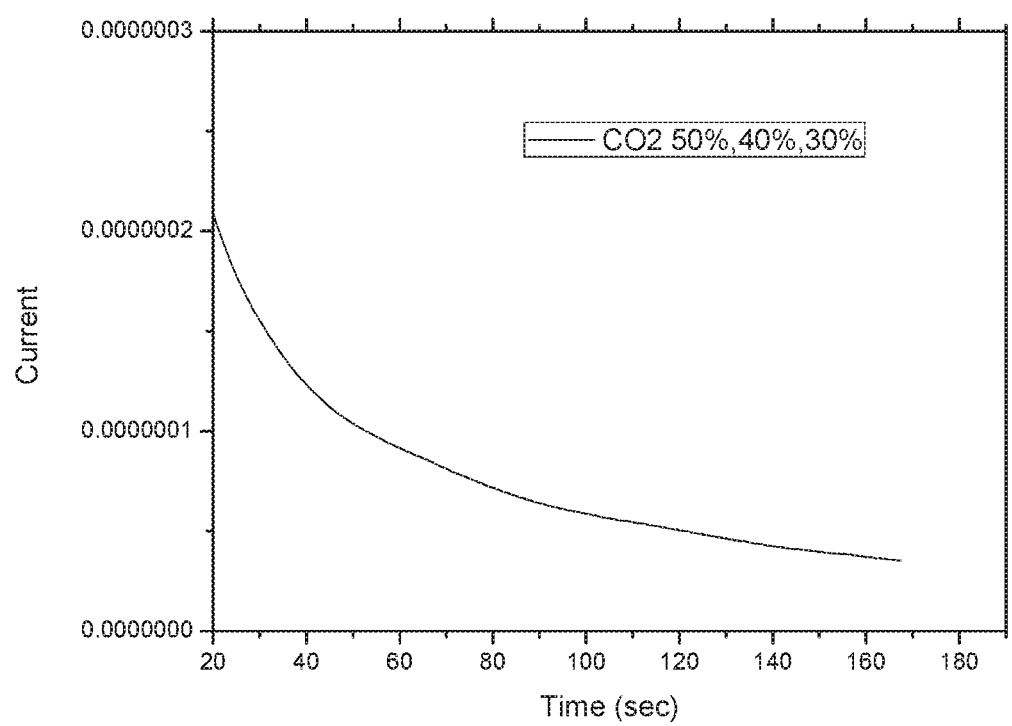
FIG. 34 shows the results of $CO_2$ control measurement and PANI-CSA on a gold finger electrode.
Figure 35:
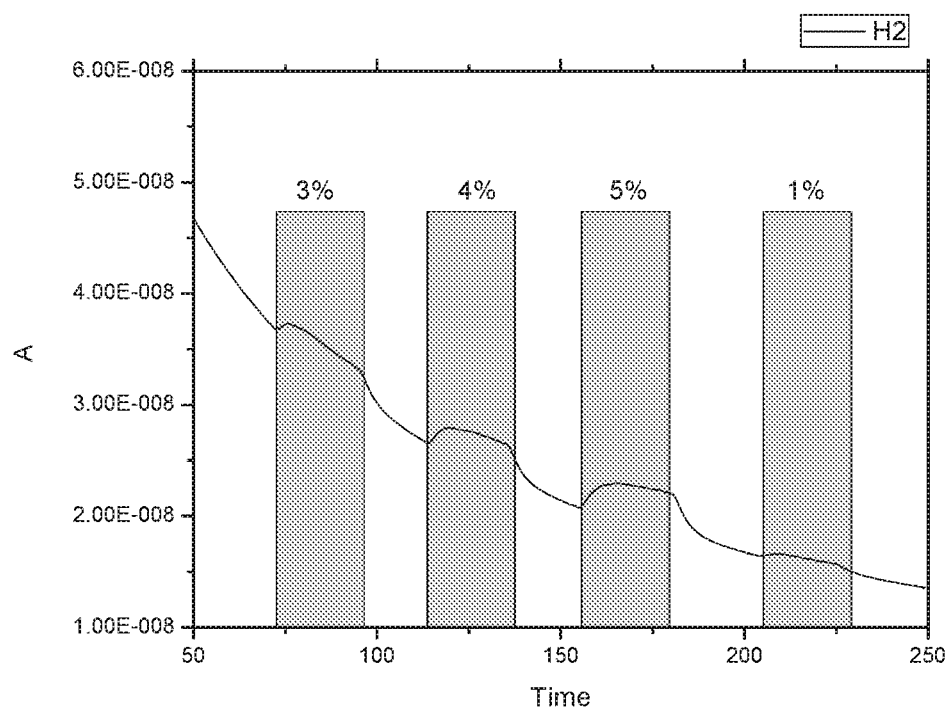
FIG. 35 shows the $H_2$ gas concentration calibration in an $N_2$ environment for a range of from 5% to 1% $H_2$.
Figure 36:
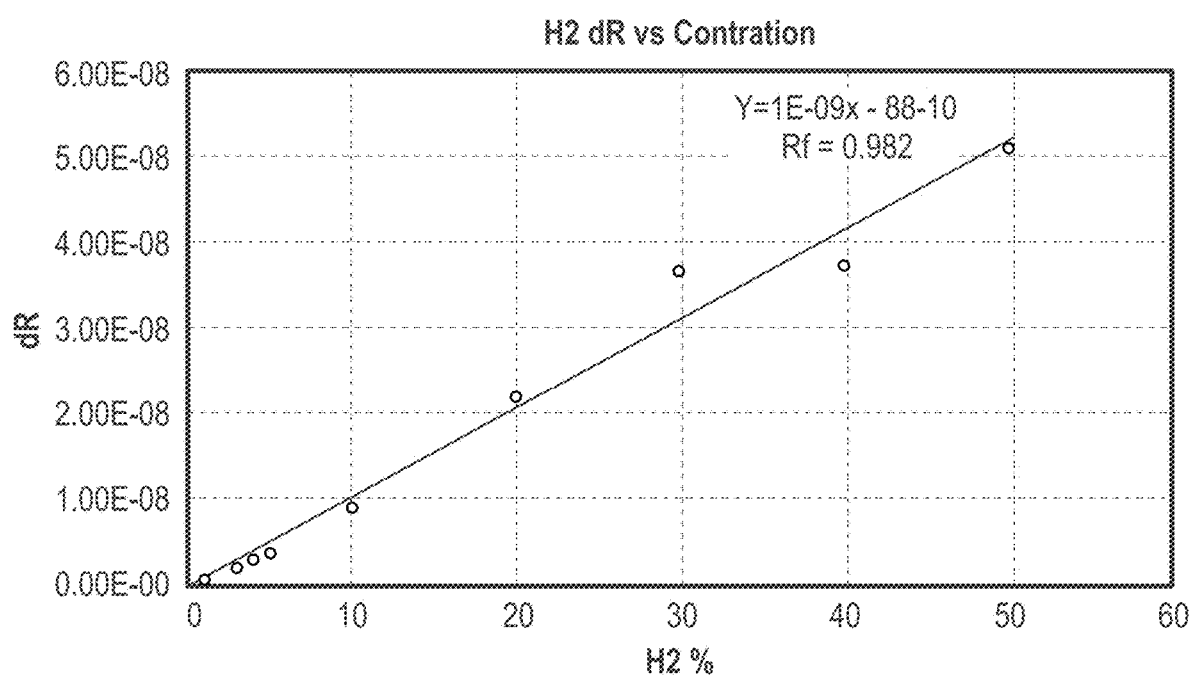
FIG. 36 shows the regression of dR for PANI response in 50%-1% $H_2$ concentration.

One volt can be applied on the gas sensor 50 and the outcome current can be measured by CH Instrument electrochemical analyzer. The analytic gas can be delivered by gas dilutor, 1010 PRECISION GAS DILUTOR, Custom Sensor Solution Inc. which provides constant flow rate and tunable ratio of two different gas samples. The control measurements can be performed to determine the individual gas affecting the PANI sensor. The results in FIG. 33 show that $N_2$ and air (where air content is about 79% $N_2$ and 21% $O_2$) are measured identically on Au-PANI sensor. The trace of other gases, like ammonia, $CO_2$, and methane insignificantly affect the circuit measurement. In FIG. 33, higher concentrations of $CO_2$ were also pumped into the sensor surface, expecting $CO_2$ to have a response on the PANI sensor. However, the sensitivity to $CO_2$ is low and the difference contributed by the presence of $CO_2$ is negligible.

Transportation of Gas to Biosensor

Precision gas diluter Model 1010 from Custom Sensor Solutions was used to transport the analytic gas into sensor chamber. Tedlar bags (5 L, prest-O sales and 0.5 L Zefon) were used to make the required dilution with the gas diluter. Mass and volumetric flow meters (Omega Engineering, INC., Norwalk, CT), with accuracy of +/-0.8%, was connected to log the flow condition. RH-200 humidity generator (L&C Science and Technology) was used to control humidity and investigate the effect of humidity on the gas sensor 50. The humidity generator generates relative humidity ranges from 3% to 95%+/-1.0%, at temperatures from ambient to 50° C. with tunable flow rate up to 5 liters/min. All devices are controlled by attached software or LabVIEW with the connection of serial communication interface. The gas samples with a series of specific humidity were prepared into Tedlar bag and measured by sensor immediately. Amprobe THWD-5 analyzer was used to measure humidity externally (+/-3% from relative humidity 10%-90%). Teflon tubing was used to connect the gas to the flow setup to minimize any gas absorption.

Hydrogen Calibration Curve for PANI/CSA Biosensor

The standard/test gas sample was prepared and confirmed the composition using $H_2$ MicroLyzer. The QuinTron Model 12i MicroLyzer™ developed by QuinTron Instrument Company Inc. (Milwaukee, WI) based on gas chromatography (GC) can measure trace concentrations (0-100 parts per million) of hydrogen in expired (alveolar) air samples in the presence of trace amounts of other biologically-produced reducing gases with +/-5.0% accuracy.

Results and Discussion

Hydrogen Response

Hydrogen response for the electrical conductivity of the PANI/CSA film was reported. To validate, the gas sensor 50 was exposed under 1% mixture of hydrogen in nitrogen. Camphorsulfonic acid (CSA) doped polyaniline films showed a 3% decrease in resistance at room temperature, $\Delta R/R_o = -3\%$, $R_o$ is the resistance value in nitrogen condition. This response is reversible.

Figure 18:
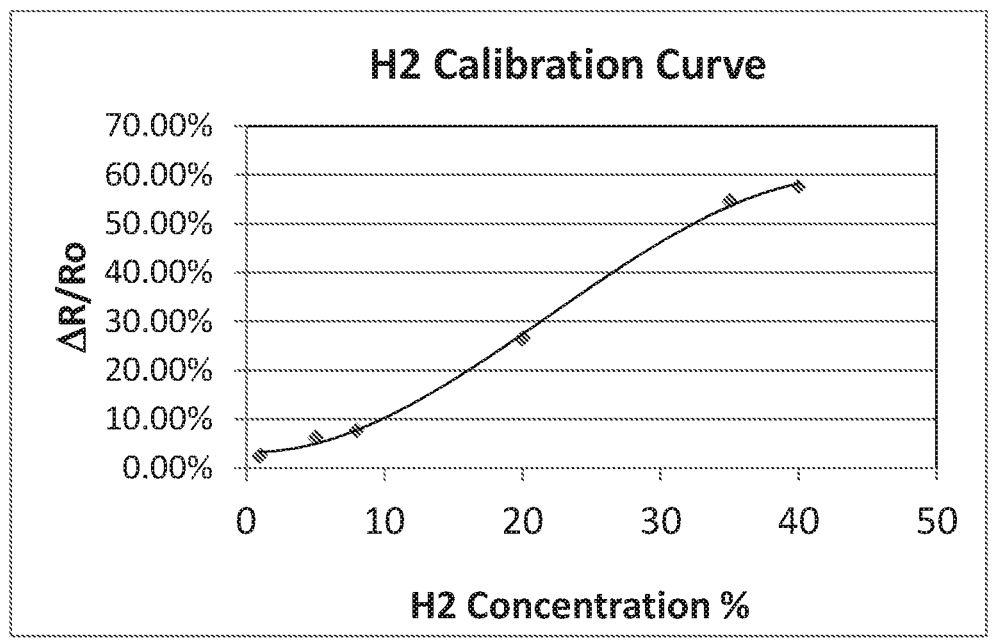
FIG. 18 is a graph showing the response of the gas sensor of the present disclosure as a function of hydrogen concentration in a nitrogen gas atmosphere.

FIG. 18 shows that the hydrogen response of the gas sensor 50 varies with the concentration of hydrogen. As can be seen from FIG. 18, the response varies monotonically with concentration, with the incremental change in response falling off at higher levels. At even higher concentrations (e.g., 30%), the hydrogen response nearly saturates and the gas sensor 50 is able to regenerate the response by purging with nitrogen for several minutes.

The Effect of Humidity for the PANI/CSA Biosensor

Figure 19:
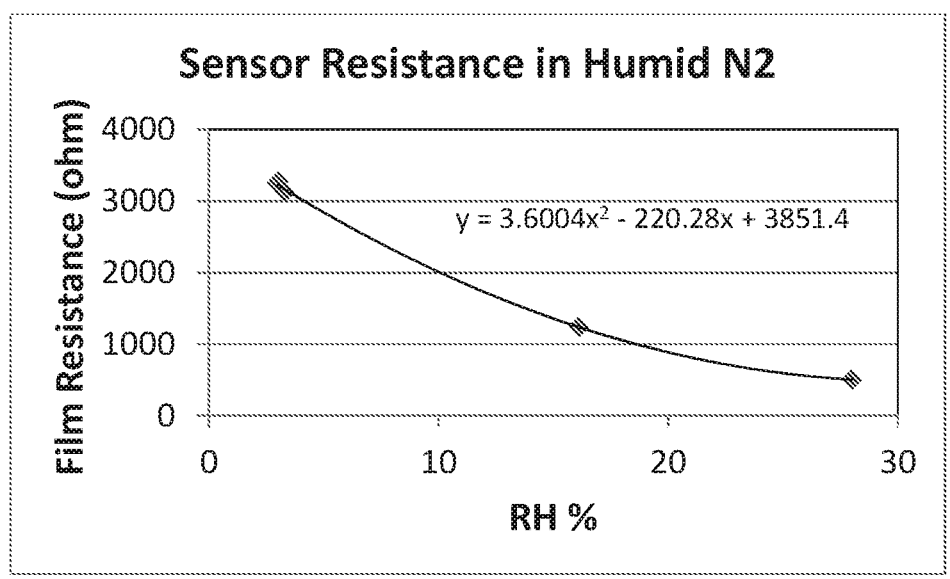
FIG. 19 is a graph showing the effect of humidity on the resistivity of the gas sensor of the present disclosure, particularly at relative humidity levels of 3-28%.

Systematic measurement of specific water content was performed in a variety of conditions, including conditions of relative humidity in a range of from 3 to 28%. The intrinsic resistance of the gas sensor 50 is linearly correlated to humidity as shown in FIG. 19. When water reversibly binds to polyaniline, polyaniline becomes more electrically conductive, which may interfere with hydrogen's interaction with polyaniline.

Figure 20:
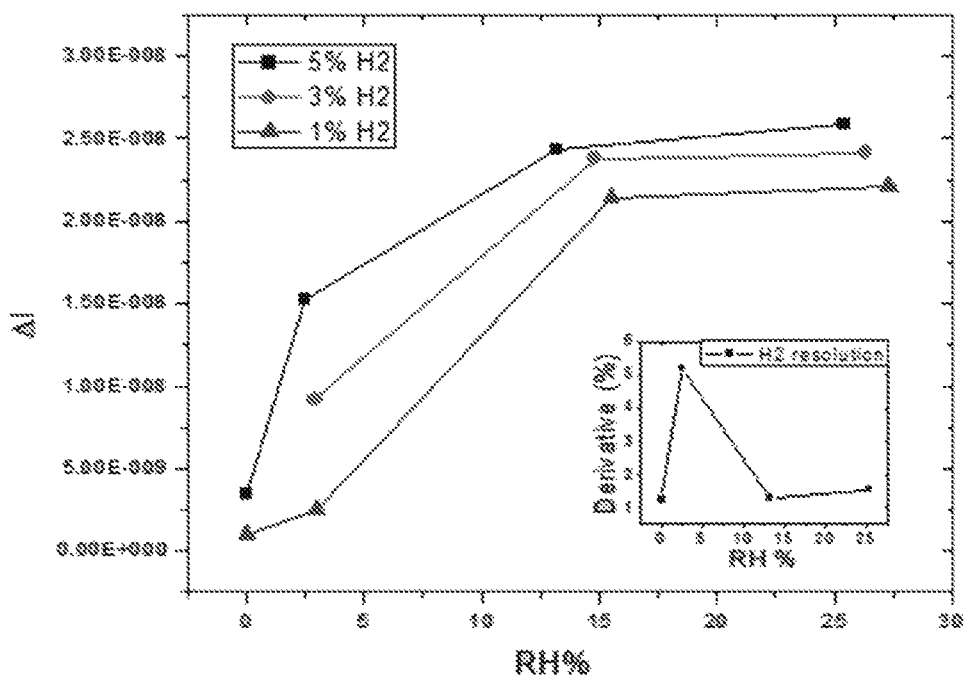
FIG. 20 is a graph showing the hydrogen gas response of the gas sensor of the present disclosure as a function of humidity.

The interference of humidity with $H_2$ measurements corresponds to the amount of water absorbed on the surface of the film. Interaction between $H_2O$ and $H_2$ also affects the surface of polyaniline. In FIG. 20, the same gradient of three different concentrations of $H_2$ was characterized in several conditions of different relative humidity, and the result indicates the reduction of $H_2$ sensitivity in the presence of water. The range of RH (relative humidity) is controlled within 28%. The conductivity change is proportional to the concentration of $H_2$ in all conditions (compared vertically). The degree of resistance change is increased by humidity and reaches steady state after ~13% relative humidity (RH). The resolution of $H_2$ is optimal in ~5 RH %

FIG. 31 shows the ability of the gas sensor 50 to measure the correct hydrogen gas concentration, where the desired hydrogen concentration is 0.5 wt %.

Figure 39:
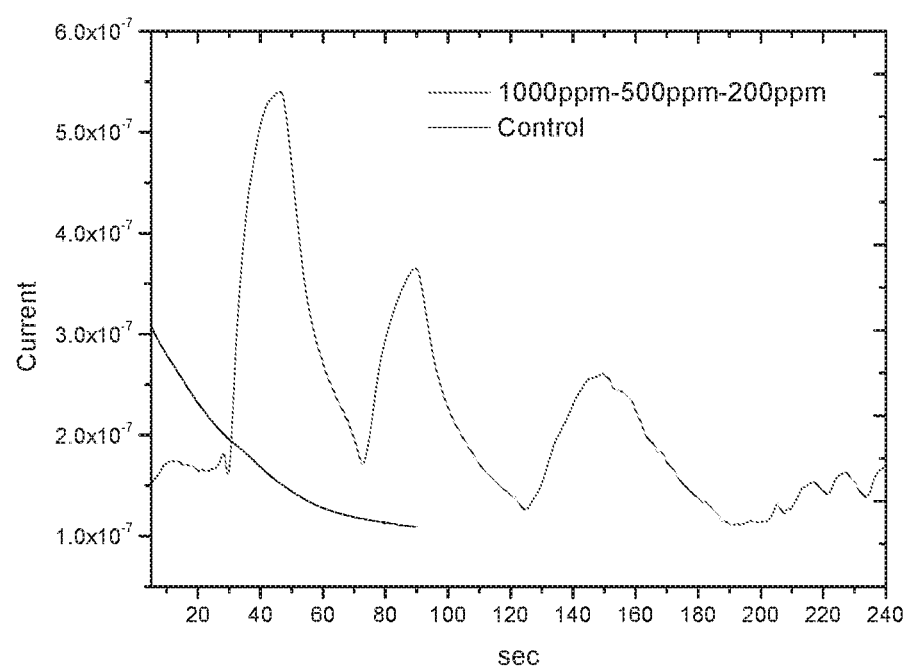
FIG. 39 shows that $H_2$ sensitivity is limited in humid $N_2$.

FIG. 39 shows the Hz gas having no water content. After mixture, the humidity would slightly change but it can be negligible according to the control measurement (short curve).

Figure 42:
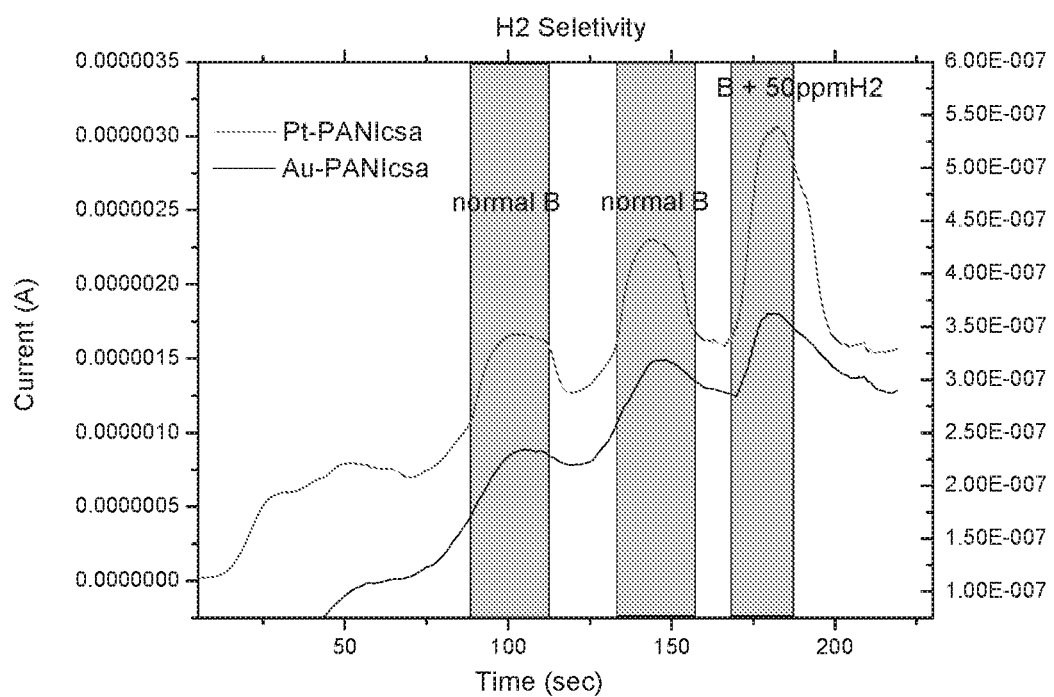
FIG. 42 shows hydrogen selectivity for breath, both with and without the addition of hydrogen gas.
Figure 43:
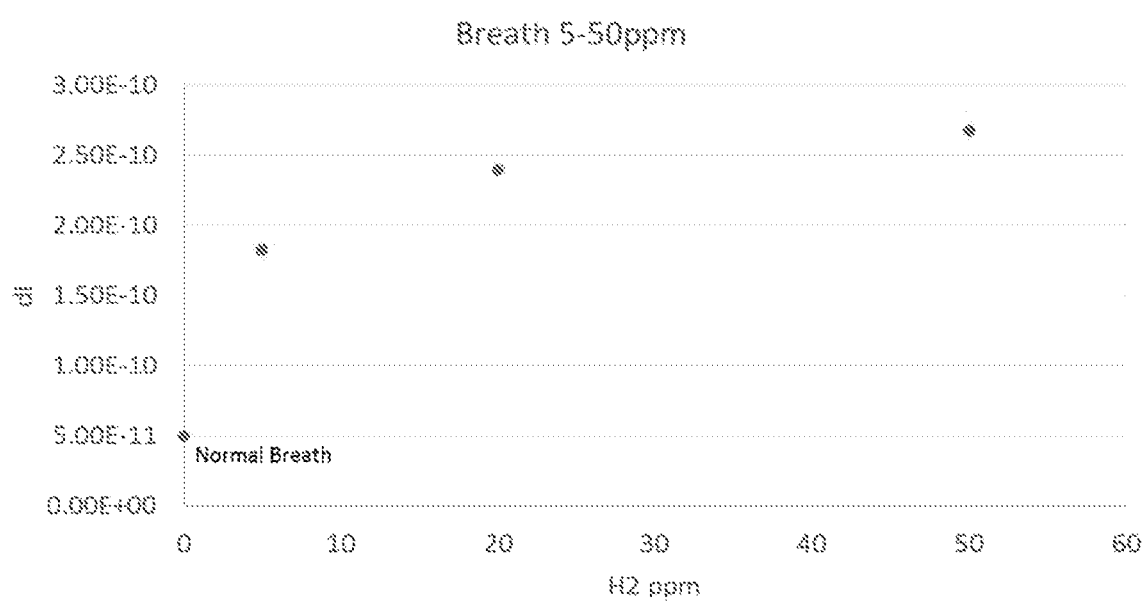
FIG. 43 shows a calibration curve of 5-50 ppm Hz, where the point at 0 ppm shows normal breath.
Figure 44:
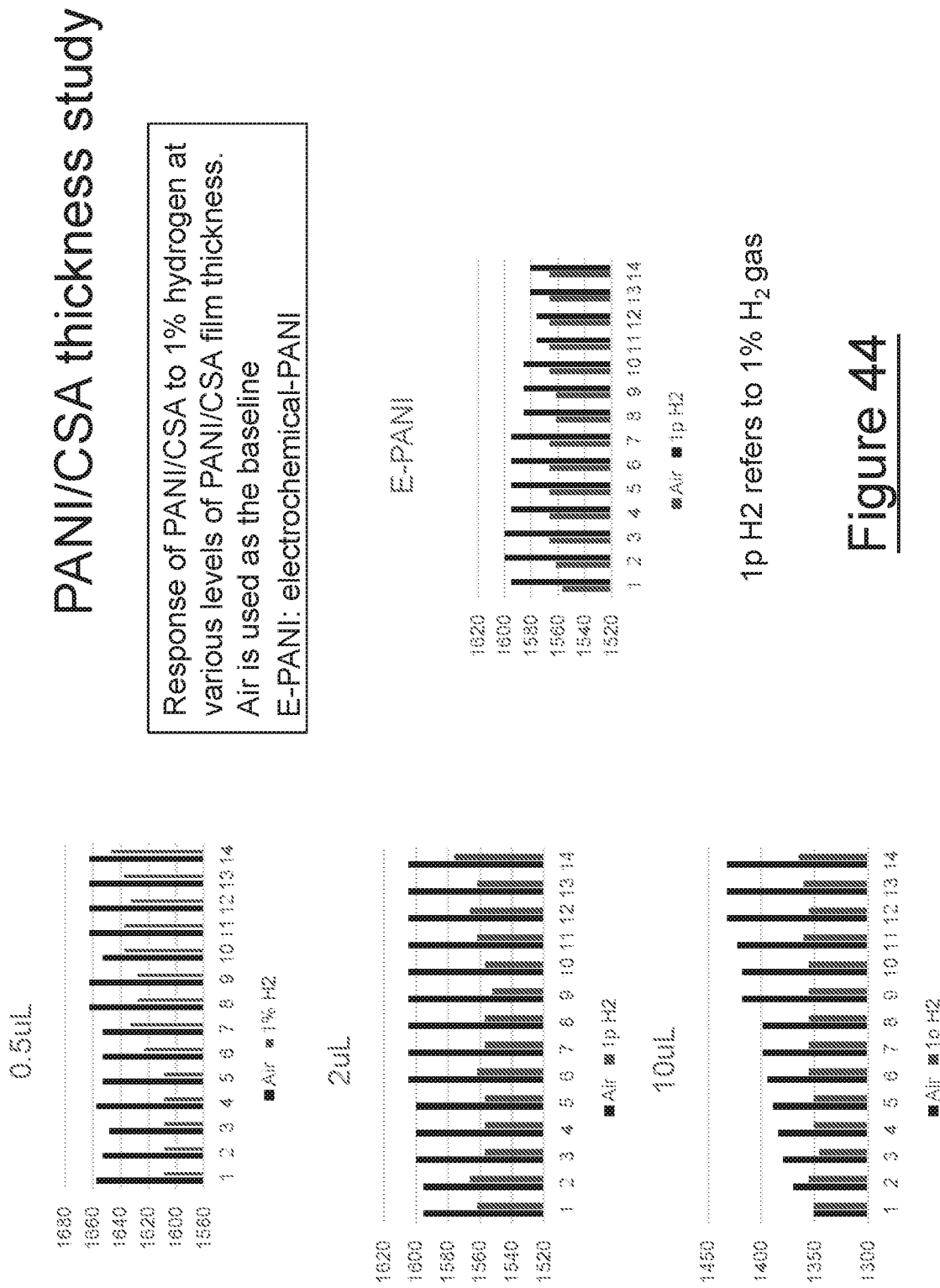
FIG. 44 shows the hydrogen gas response of a PANI/CSA sensor at various levels of PANI/CSA film thickness (i.e., at 10 μl, 2 μl and 0.5 μl) and when PANI is electrochemically polymerized (where the lower the thickness, the higher the response of the PANI/CSA to hydrogen gas).
Figure 45:
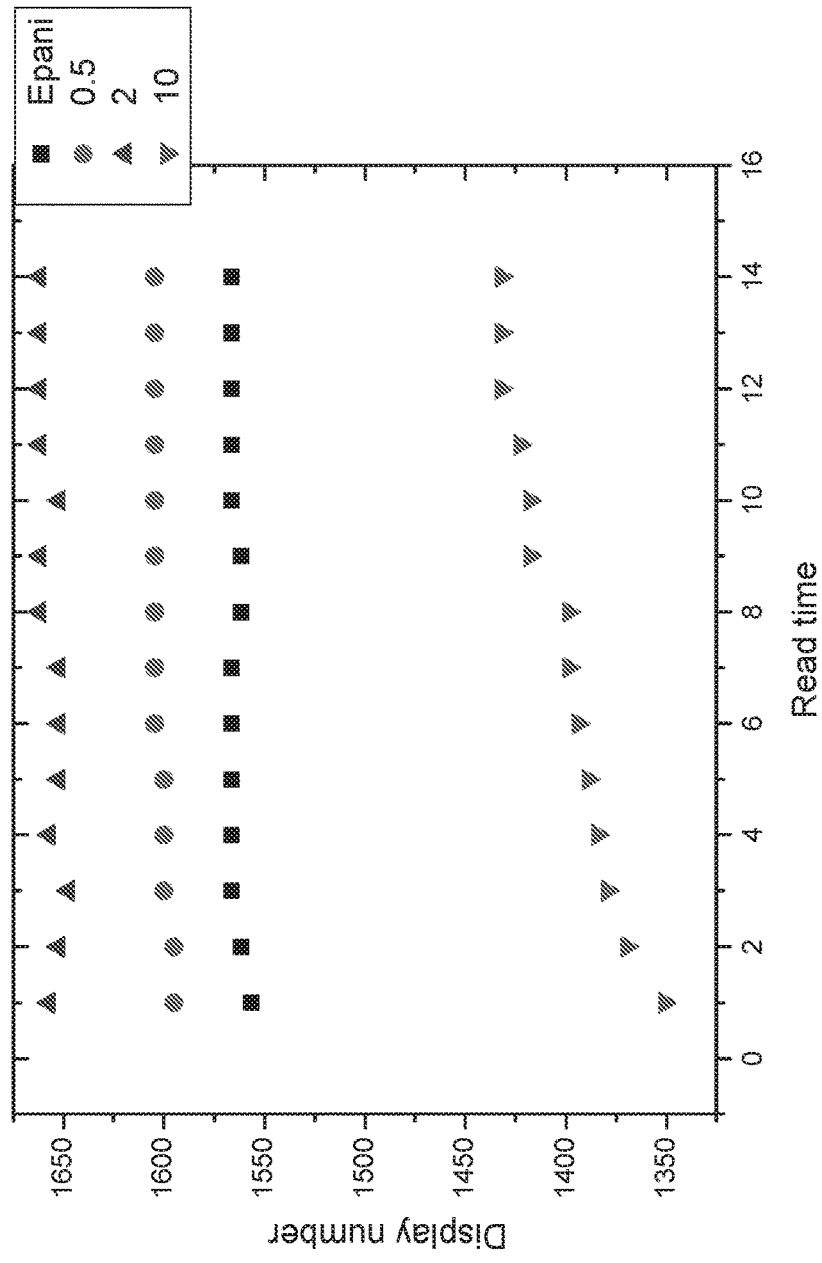
FIG. 45 shows the stability of PANI/CSA films at various thickness levels when 1% concentration of hydrogen gas is applied, where the E-PANI sensor is stable and the thicker film (10 μl) is the least stable.
Figure 46:
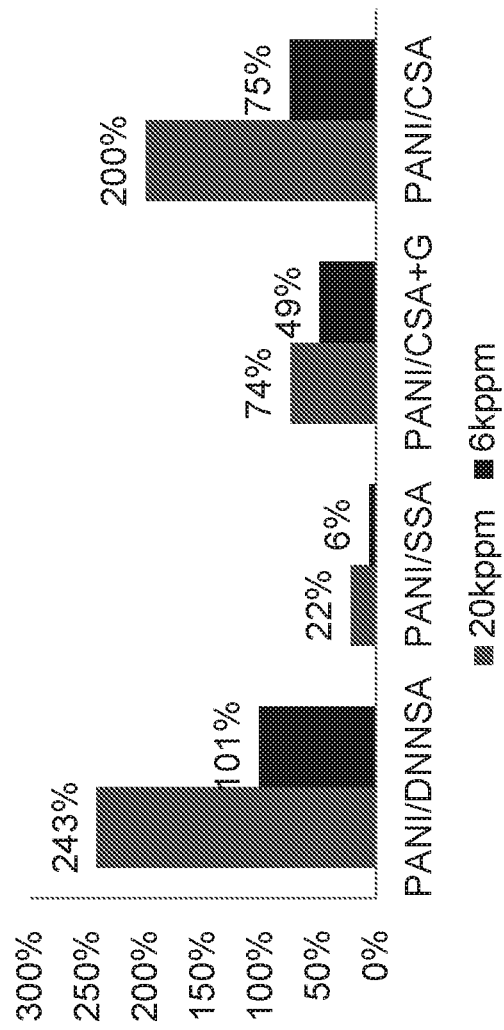
FIG. 46 shows the response of different PANI doped sensors of the present disclosure (i.e., a PANI sensor doped with DNNSA, a PANI sensor doped with SSA, a PANI sensor doped with CSA, and a PANI sensor doped with CSA and graphene) when exposed to two concentrations of hydrogen gas, including 20 kppm (20,000 ppm) and 6 kppm (6,000 ppm), where the PANI/DNNSA sensor demonstrates the highest response to hydrogen gas.
Figure 47:
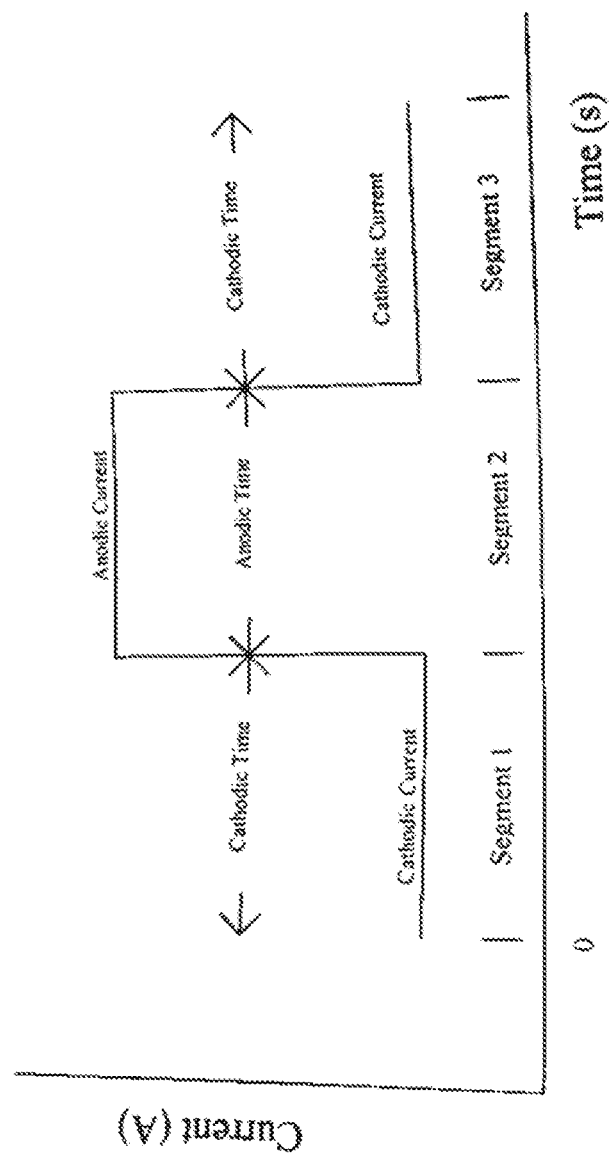
FIG. 47 shows the stages of an electrochemical polymerization process in accordance with certain embodiments of the present disclosure.

Referring to FIG. 42, Normal B is breath without addition of Hz gas; B+ 50 ppm H is a mixture of normal breath plus 50 ppm of $H_2$. Pt-PANI sensor response is the top line and Au-PANI sensor response is shown on the bottom line.

Other Effects

Figure 21:
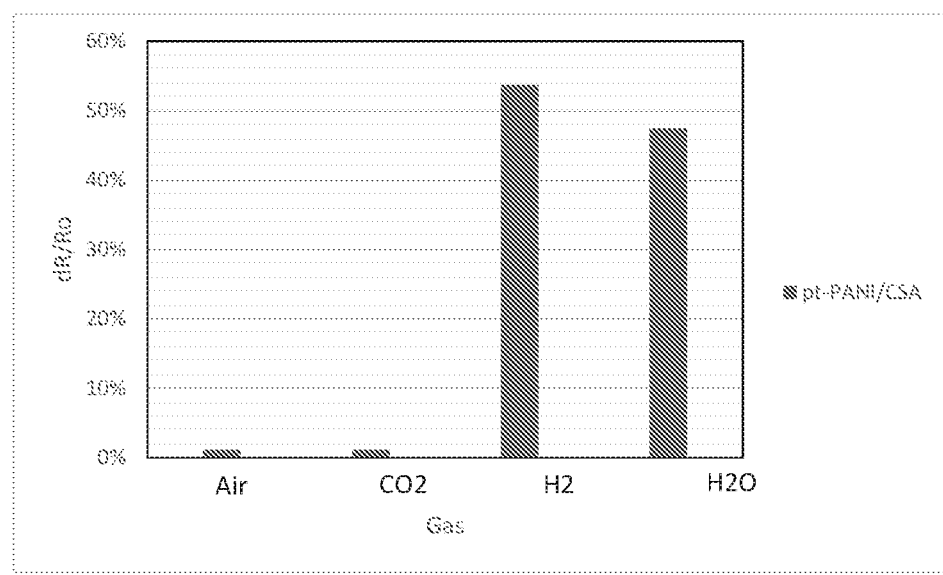
FIG. 21 is a graph showing the sensitivity of the PANI/CSA sensor of the present disclosure to particular gases.

Carbon Dioxide has no significant effect on the response of the nanofibers sensor 50. FIG. 21 shows the sensitivity of the gas sensor 50 from various gases. The gas sensor 50 was tested at normal carbon dioxide concentrations (4%). Within experimental error, the response is the same and therefore carbon dioxide has no effect on the sensor response. This is unlike many hydrogen sensors, which are strongly sensitive to the presence of carbon dioxide and oxygen.

Algorithms are incorporated into the breath analyzer 10 as software and used to convert electrical current to concentration of hydrogen gas (measured in ppm of hydrogen).

Breath Characterization

Figure 22:
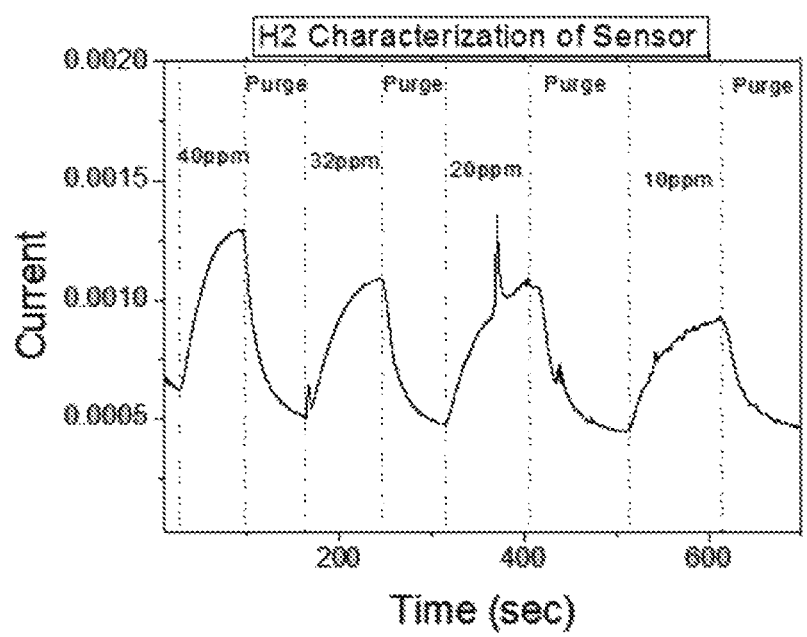
FIG. 22 is a graph showing the current signals of the PANI/CSA sensor of the present disclosure when exposed to various gases.
Figure 23:
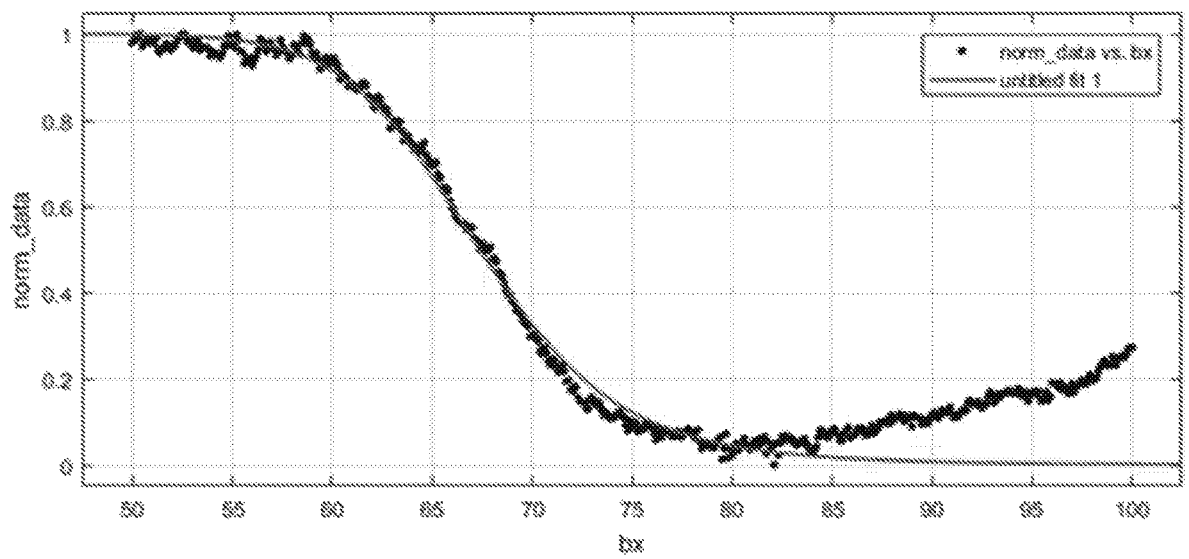
FIG. 23 is a graph showing the fitting result for amperometric i-t measurement.

Upon exposure to a series of mixtures of hydrogen in standard breath, in the range of 10 to 40 ppm, CSA doped polyaniline film shows 30% decrease in resistance at room temperature, $\Delta R/R_o = -40\%$ in FIG. 22, where $R_o$ is the resistance of film exposed in standard breath and $\Delta R = R_m - R_o$, $R_m$ is the resistance of the film exposed in mixture. The response is reversible by purging with nitrogen for several minutes. The response curve is fit with kinetic absorption equation (Equation 2 below), yielding two parameters corresponding to slope and increase and saturated value of the absorption. The illustration of fitting is shown in FIG. 23.

$$A = \frac{ke^{\left(\frac{-(a-bt)}{c}\right)}}{1+ke^{\left(\frac{-(a-bt)}{c}\right)}} \quad \text{Equation (2)}$$

Figure 24:
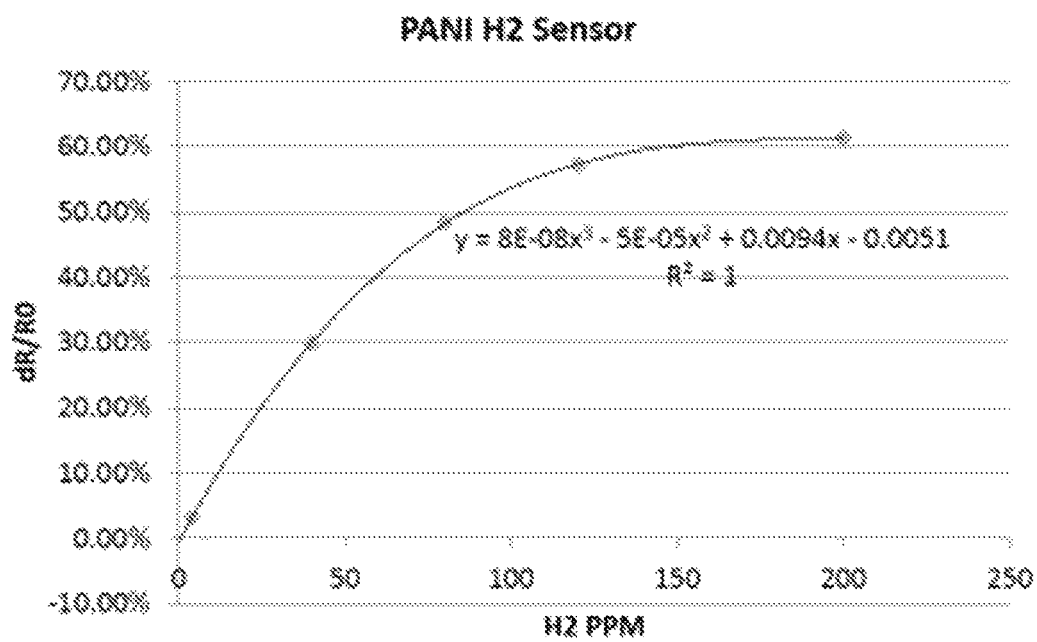
FIG. 24 is a graph showing the resistivity response of the PANI/CSA sensor of the present disclosure as a function of hydrogen concentration detected within a range of from 1-200 ppm.

FIG. 24 shows that the response corresponds to the concentration of Hz in breath in the constant temperature. A wide variety of equilibrium isotherm models (Langmuir, Freundlich, Brunauer-Emmett-Teller, Redlich-Peterson, Dubinin-Radushkevich, Temkin, Toth, Koble-Corrigan, Sips, Khan, Hill, Flory-Huggins and Radke-Prausnitz isotherm) have been formulated in terms of three fundamental approaches. The derivation of the isotherm modeling provides the approach of physical interpretation based on the model parameters used. For the present device 10 and method, polynomial fitting also shows high agreement with the measurements.

5-50 PPM of Hydrogen Detection by Gas Sensor 50

Figure 7:
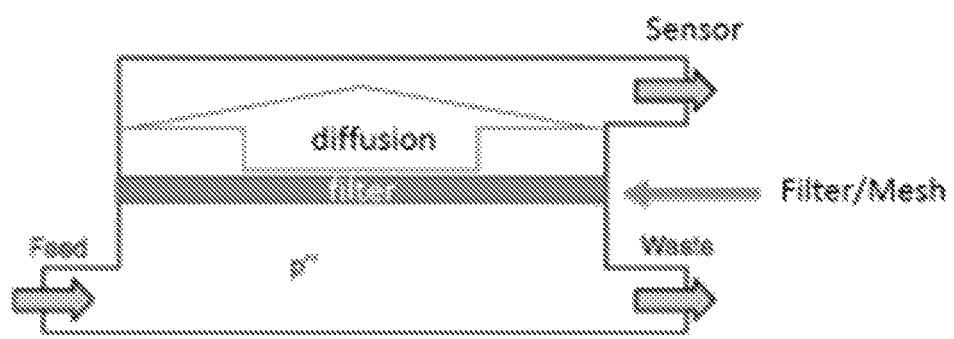
FIG. 7 is a schematic illustrating the flow of air through an embodiment of a breath analyzer of the present disclosure.
Figure 37:
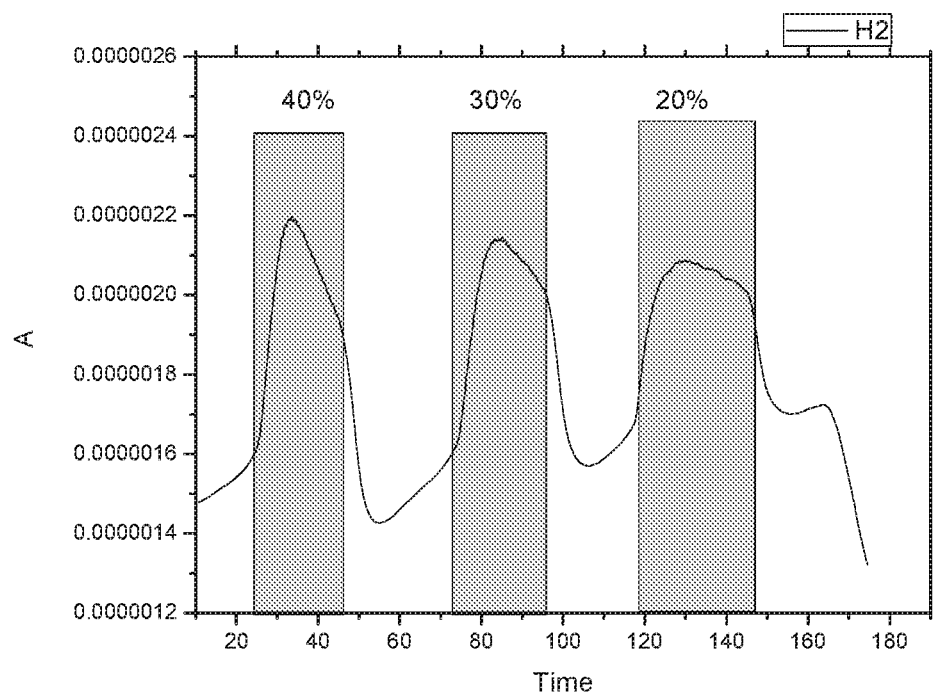
FIG. 37 shows the effect of $H_2$ gas in a humid $N_2$ environment.
Figure 38:
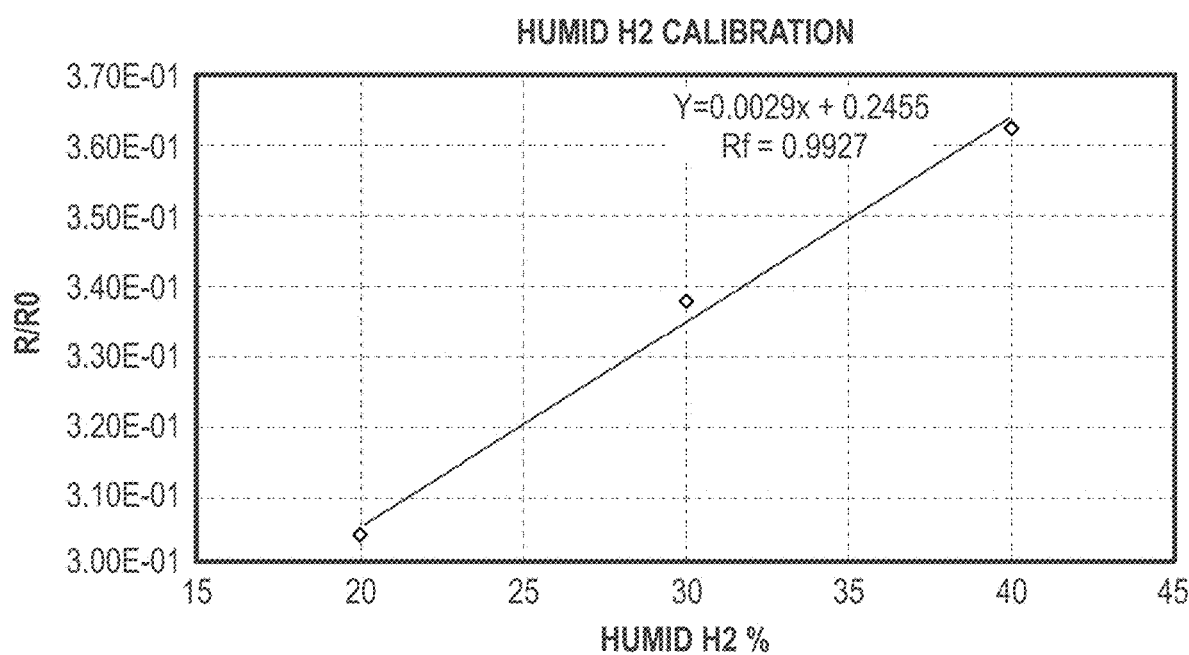
FIG. 38 shows a regression curve for $H_2$ detection in humid $N_2$ environment.

The varied concentrations of $H_2$ gas were first measured on Au-PANI sensor 50 of the present disclosure in a pure $N_2$ environment. The pure hydrogen gas was diluted by $N_2$ to 5% to 1% (50000-10000 ppm), which showed 20% dR/R0 change rate in FIGS. 6 and 7, which summarized the $H_2$ calibration curve for 50% to 1% $H_2$. After regression, the $H_2$ minimum measurement value could be limited. A further improvement was proposed with a platinum (Pt) electrode and introduced humidity. In the presence of humidity, the sensitivity of Pt-PANI is improved 150% dR/R0 difference of 200 ppm $H_2$, as shown in FIG. 39. The water increases the general conductivity of PANI film on the Pt electrode, which also enhances the resistance effect by $H_2$. The preliminary data are shown in FIGS. 37 and 38 as well. As shown in FIG. 39, when humidity is present the difference in $H_2$ concentration between dry and humid conditions is 1 ppm. Water (humidity) increases the conductivity of PANI on a platinum (Pt) electrode and therefore the sensitivity of PANI to $H_2$ gas.

The present disclosure also includes a method for detecting hydrogen gas to determine the presence of a gastrointestinal disorder in a subject's digestive tract. By using the device 10 and method of the present disclosure, hydrogen gas in the range of 1-100 ppm (e.g., 1-80 ppm, or 1-50 ppm, or 1-20 ppm, or 1-10 ppm) in a human breath sample can be detected.

In one non-limiting embodiment, the subject utilizes the device 10 as follows:

1. Using the on/off switch 68, the subject turns the device 10 on, and the display 70 provides an indication (e.g., light, numbers, and/or characters) that the device is ready to be used.
2. The user presses continuously and steadily on the press/release button 67 (e.g., using an index finger or thumb). The subject holds the press/release button 67 for the length of the subject's exhalation through the mouthpiece 12 and into the device 10. During the time that the press/release button 67 is pressed, the display 70 may show multiple numbers continuously, or no numbers, or nothing at all.
3. At the end of the exhalation through the mouthpiece 12 and into the device 10, the subject releases the press/release button 67.
4. After the release of the press/release button 67, in a short period of time (e.g., a few seconds), the display 70 will display the current generated, or the concentration of hydrogen (measured in ppm), or the words "positive" or "negative", or colors indicating positive or negative. The positive or negative indication corresponds to whether the subject is positive or negative for a particular gastrointestinal disorder.
5. Thereafter, the subject turns off the device 10 through the on/off switch 68.

In another non-limiting embodiment, there is no external press/release button 67. Instead, the press/release function of the device is performed internally by the device itself. In this embodiment, the subject utilizes the device 10 as follows:

1. Using the on/off switch 68 the subject turns the function of the device on and the display displays light and numbers or characters indicating that the device is ready to be used.
2. Placing the mouth around the mouthpiece 12, the subject exhales into device 10. At the end of the exhalation through the mouthpiece 12 and into the device 10, the subject removes the lips from the mouthpiece 12.
3. After the end of the exhalation, the display 70 will display the current generated or the ppm of hydrogen, or the words positive or negative or colors indicating positive or negative.
4. After the utilization of the device 10 is completed, the subject turns off the device 10 through the on/off switch 68.

In one example, human breath mixture was prepared using normal breath mixed with Hz at the desired concentration. A molecular sieve (MS) filter was used, and the background gas was relative humidity (RH) 30% $N_2$. Pt-PANI and Au-PANI were used simultaneously for comparison. FIG. 41 shows the result when adding 50 ppm $H_2$ in normal breath. Pt-PANI is apparently able to distinguish the difference of $H_2$ content in ppm scale, meanwhile, Au-PANI shows less of a response to the mixture of normal breath and 50 ppm $H_2$ breath, as summarized in Table 4. A further characterization with different $H_2$ concentrations in normal breath (50-5 ppm) was also performed and is shown in FIG. 42.

TABLE 4

The resistance responses in Pt and Au based sensor to H2 and breath

| | Electrode | | | |
| --- | --- | --- | --- | --- |
| | Pt-PANI | | Au-PANI | |
| Gas | Breath | H2 | Breath | H2 |
| R/Ro | 111% | 199% | 68% | 75% |

Example 1: Sample Assay for Detection

Figure 25:
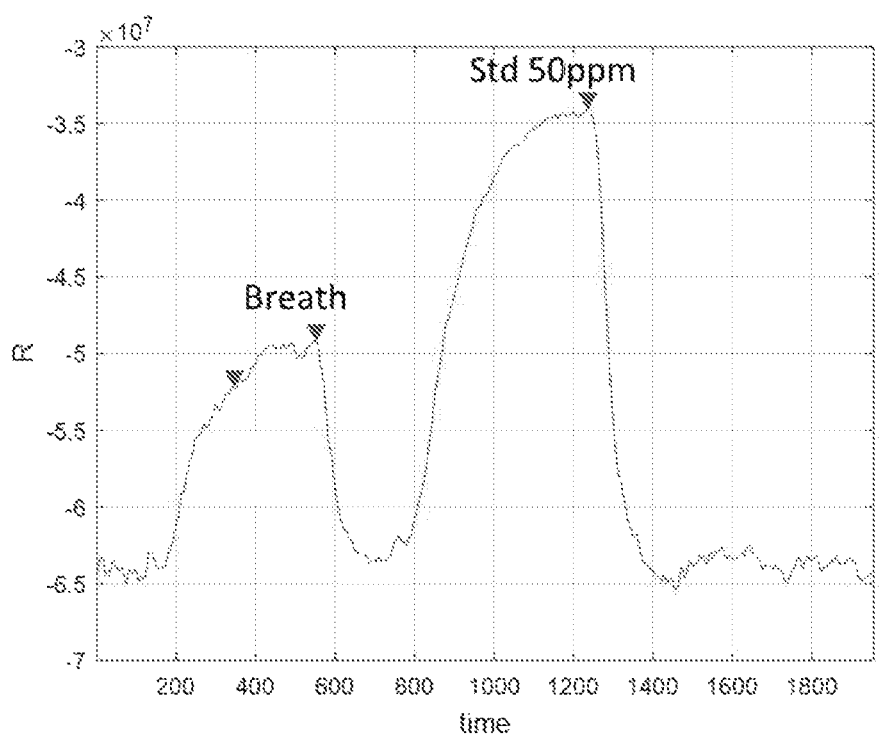
FIG. 25 is a graph showing the raw data of a breath sample measured with the gas sensor of the present disclosure, where the identified peak corresponds to the amount of hydrogen gas.
Figure 26:
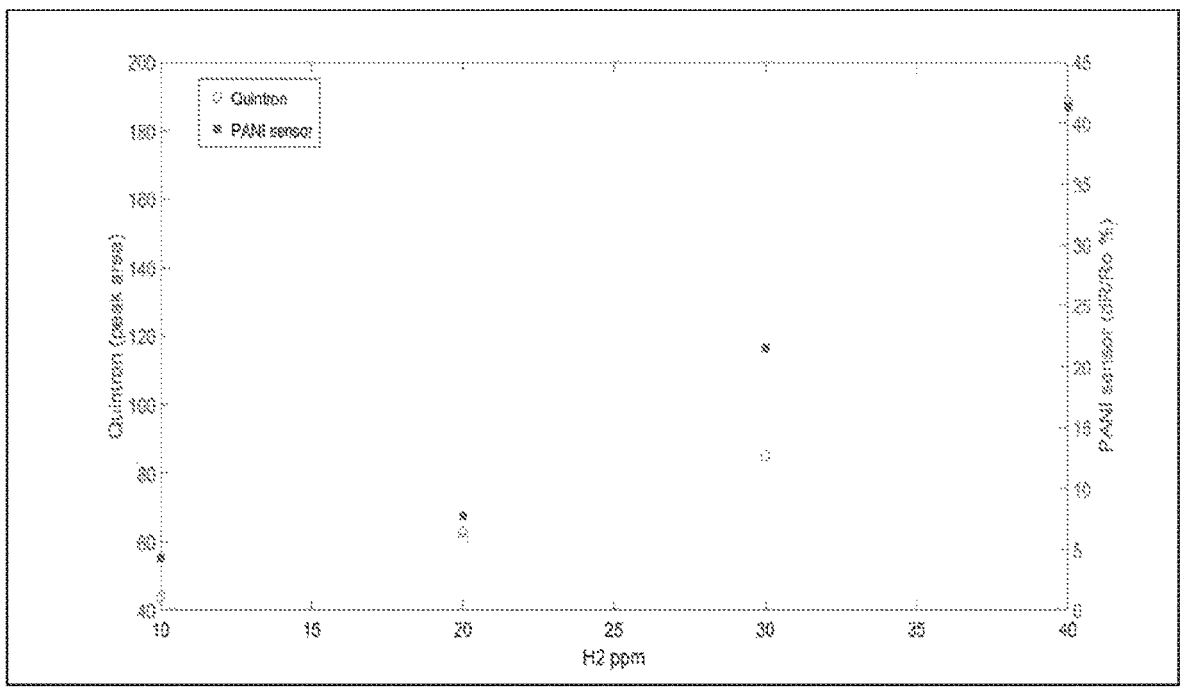
FIG. 26 is a graph showing the comparison of hydrogen gas characterization with the gas sensor of the present disclosure and Quintron.

Patients abstain from food and drink except for small quantity of water for at least 8 hours before this test. A breath sample is delivered to the hydrogen biosensor as below:
Step 1: Collect breath sample in Tedlar bag.
Step 2: Breath is delivered to biosensor using dilutor in the 0.1 L/min flow rate.
Step 3: Electronic data is taken until signal is stable within 2 minutes.
Step 4: Two known concentrations of hydrogen gas in breath are used to generate the calibration curve for the biosensor.
Step 5: Customized program is used to perform the modeling and to calculate the hydrogen gas concentration.
Result An example result is shown in FIG. 25, where the amount of hydrogen gas is 5.2 ppm with a variance of 5%.

Example 2: Sensor Validation Using Quintron

This example describes the comparative analysis of a breath sample with a commercial device, Quintron, and the hydrogen gas polyaniline biosensor of the present disclosure.

The same breath sample of Example 1 was also characterized using Quintron, and the measuring value is consistent with gas sensor 50. The deviation of two devices, Quintron and biosensor, is ~0.12%.

Example 3: Breath Analyzer

Figure 27:
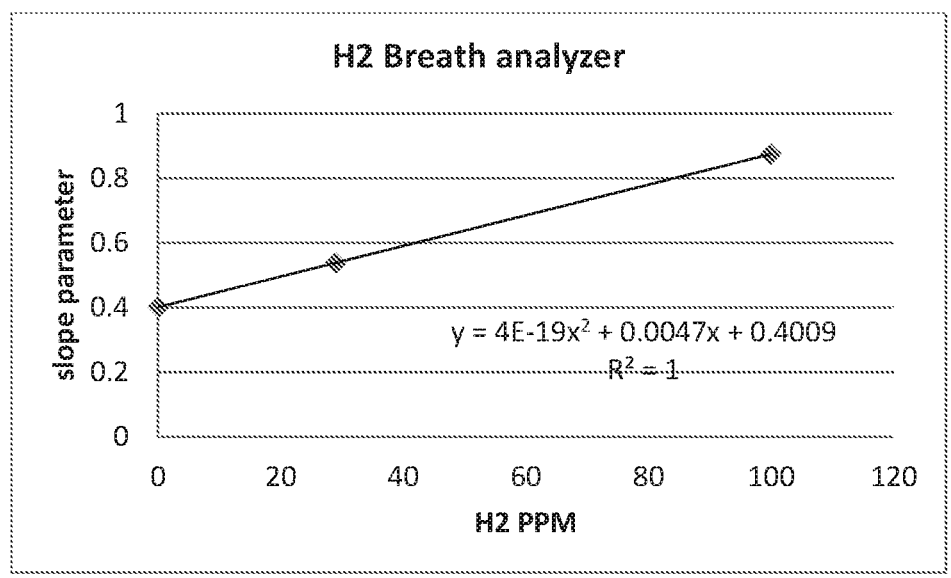
FIG. 27 is a calibration curve for the breath analyzer of the present disclosure.
Figure 28:
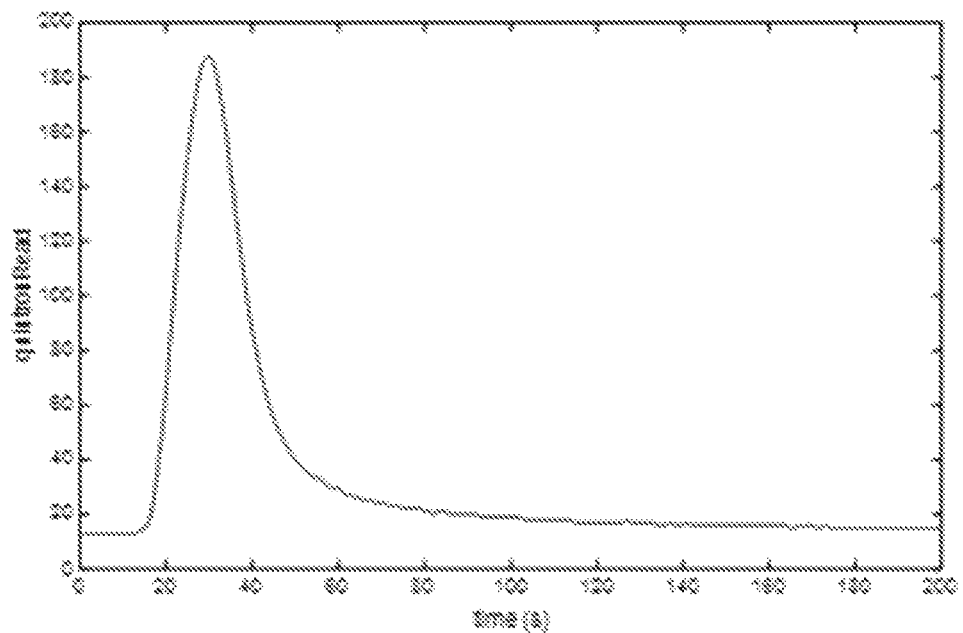
FIG. 28 shows an example of Quintron data that can be recorded in a computer and analyzed for peak values and peak areas.
Figure 29:
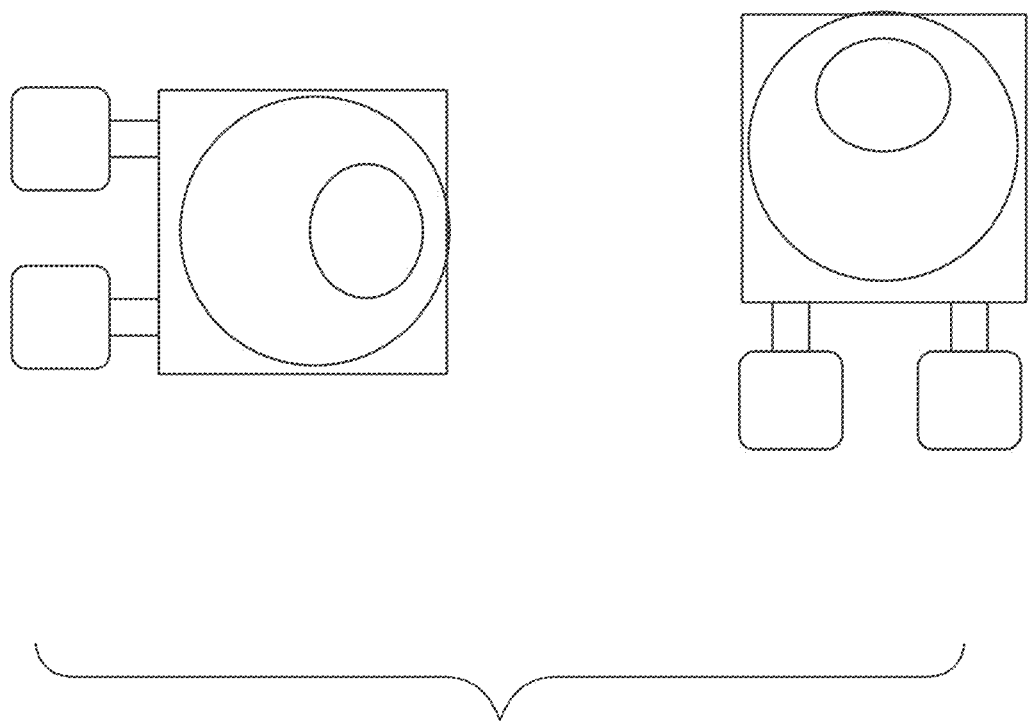
FIG. 29 shows an embodiment of PANI fabricated by a spin coat to create a uniform film.
Figure 30:
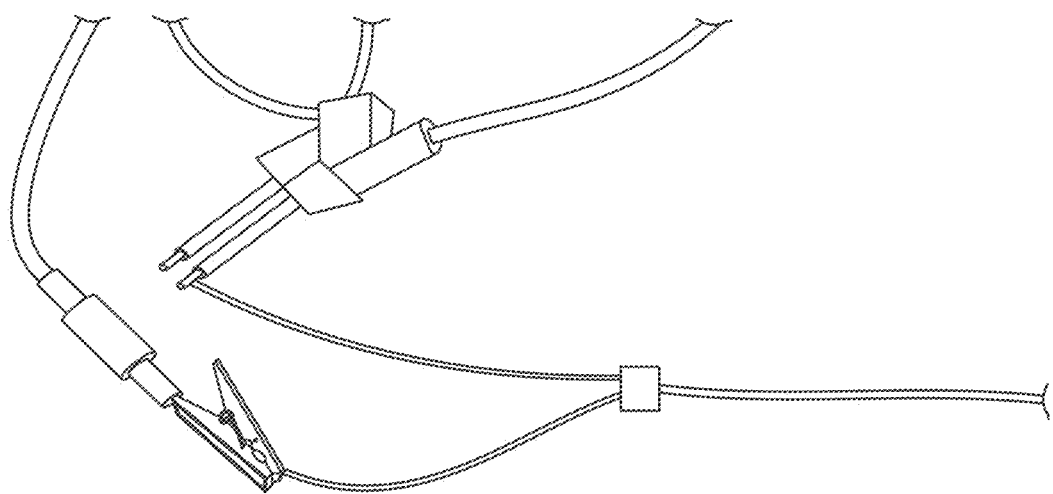
FIG. 30 shows an embodiment of a breath analyzer of the present disclosure having soldered wires connected with sensor electrodes.

A standalone breath analyzer using PANI/CSA/Pt (Pt=platinum) biosensor was built and tested. The structure of the breath analyzer 10 contains a flow system regulating breath flow and humidity for the gas sensor 50 using a desiccant/breath filter, a real-time LED display 70 for displaying results from the gas sensor 50, a gas sensor 50 mounted behind the desiccant/breath filter, and an arduino microchip to acquire data and analyze. Three breath samples were tested and able to establish a relationship curve for $H_2$ detection. The curve was fitted with a $2^{nd}$ order polynomial equation as a function of change in slope due to the breath sample (FIG. 27). Equation 3, shown below, can be used, which will allow display 70 to display the hydrogen gas concentration present in the breath sample tested.

$$ppm \to \frac{-a2 - \sqrt{a2^2 - 4a1a3 + 4a1\text{slope}}}{2a1}, \qquad \text{Equation 3}$$

where a1=4E-19, a2=0.0047, a3=0.4009

Figure 48:
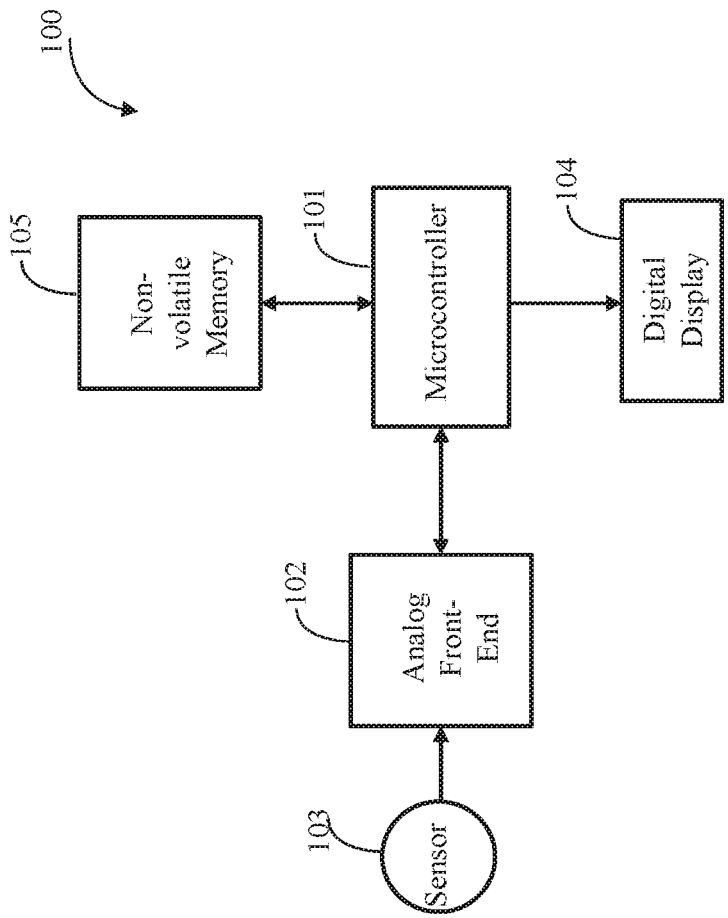
FIG. 48 shows a schematic diagram of universal readout system that includes a sensor, an analog front-end circuit, a microcontroller, a digital display, and a non-volatile memory.

The system shown in FIG. 48 provides a universal readout circuit system 100 for sensors that includes an analog front-end circuit 102, one or more sensors 103, a microcontroller 101, a digital display 104, and a non-volatile memory 105. The system 100 can further include a Universal Serial Bus (USB) port to communicate with a Personal Computer (PC) for updating firmware, as well as for communicating data such as sensor readouts, and patient ID between the PC and the system. The one or more sensors 103 can be any type of sensor, e.g., electrochemical (polymer-based) sensor, electrothermal sensor, metal oxide sensor, metal oxide combined with nanostructure sensor, field effect transistor (FET) sensor, optical sensors, and other types of sensors.

FIG. 48 shows a universal readout circuit for sensors and is designated generally by reference numeral 100. The sensor 103 senses a chemical quantity, such as gases contained in human breath, and can include such gases as hydrogen, ammonia, nitrogen, nitric oxide, $CO_2$, $^{13}CO_2$, acetone, methane and/or volatile organic compounds (VOCs). The analog front-end circuit 102 transduces this chemical quantity into an electrical quantity such as electric current or electrical potential. In one embodiment of this disclosure, the analog front-end circuit 102 may comprise a voltage regulator (for providing a fixed voltage), a resistor, and wires or printed circuit traces to connect this resistor and power source to the sensor. The analog front-end circuit 102 may additionally comprise amplification, filtering, and/or signal conditioning circuits.

The electrical signals from the analog front-end circuit 102 are connected to the microcontroller 101. The microcontroller 101 may be a standalone integrated circuit such as a microchip PIC microcontroller or it may be on a pre-built commercially available printed circuit board (e.g., it may be an Arduino Uno).

One or more non-volatile memory 105 may be connected to the microcontroller 101, which may be used to store and recall the firmware to be executed on the microcontroller 101. The non-volatile memory 105 may also be used to store and recall the digitized sensor data and other meta data. For instance, in one embodiment of this disclosure, such data may include patient information. One or more of the non-volatile memory 105 in the system may be a flash memory chip, which may or may not be integrated inside the microcontroller 101. One or more of the non-volatile memory 105 may also be a Secure Digital (SD) card.

A digital display 104 may also be connected to the microcontroller 101. The digital display 104 may be used to display step-by-step instructions on how to use the device, sensor readout results, error codes or messages if the device enters an error state or other pertinent information for operation of the device. In one embodiment of the disclosure, the digital display 104 may show information about the patient. The universal readout circuit system 100 receives power from a power source, which may be any source of power (e.g., a lithium ion battery, any type of battery, or power provided from a PC via the USB port).

While some preferred embodiments of the invention have been described, it should be understood that various changes, adaptations and modifications may be made therein without departing from the spirit of the invention and the scope of the appended claims.

What is claimed is:

1. A handheld, portable breath analyzer comprising:
   a main body connectable to a power source and having a processor, an electrical circuit, a humidity control unit, and a hollow channel extending within the main body and being in fluid communication with a chamber disposed within the main body, the chamber is configured to receive a gas sensor, the electrical circuit operably connecting the power source to the gas sensor and connecting the gas sensor to the processor; and
   a mouthpiece removably insertable into the channel such that the mouthpiece is in fluid communication with the chamber, the mouthpiece is configured to be used by a user to exhale a breath sample into the channel;
   wherein the chamber is configured to house the gas sensor adapted to detect hydrogen gas present in the breath sample of the user, the humidity control unit being disposed adjacent to the gas sensor such that the breath sample travelling through the channel contacts the humidity control unit prior to reaching the gas sensor;
   wherein the gas sensor comprises a conductive material and a hydrogen selective material in contact with the conductive material, wherein the hydrogen selective material has a resistivity that increases in response to increased concentration of hydrogen, wherein the humidity control unit is adapted to maintain a relative humidity for the gas sensor in a range from 0.1% to 15%, wherein the hydrogen selective material comprises polyaniline, wherein the polyaniline is doped with a dopant that increases pH sensitivity of the polyaniline, wherein the dopant comprises dinonylnapthylsulfonic acid, and wherein the polyaniline has a resistivity that increases in response to increased concentration of hydrogen; and
   wherein the processor is configured to detect the resistivity of the gas sensor and calculate a concentration of hydrogen present in the breath sample of the user based on the resistivity of the gas sensor.

2. The breath analyzer of claim 1, wherein the mouthpiece has a first end that can be used by the user to exhale the breath sample and a second end that can be inserted into the channel, wherein the gas sensor, when the mouthpiece is inserted into the channel, is spaced away from the second end of the mouthpiece such that, when the user exhales using the mouthpiece, the breath sample travels out of the mouthpiece through the channel and into the chamber, and wherein the polyaniline has a pH sensitivity of more than 59 mV.

3. The breath analyzer of claim 1, wherein the dopant consists essentially of dinonylnapthylsulfonic acid.

4. The breath analyzer of claim 1, wherein the conductive material comprises a plurality of electrodes.

5. The breath analyzer of claim 4, wherein the plurality of electrodes comprises interdigitated finger electrodes.

6. The breath analyzer of claim 1, wherein the hydrogen selective material is deposited as a film on the conductive material.

7. The breath analyzer of claim 1, wherein the humidity control unit is a desiccant or a filter, and wherein the gas sensor is disposed along a pathway of the breath sample exhaled by the user and behind the desiccant or filter.

8. A handheld, portable breathalyzer comprising:
   a main body having a humidity control unit and a hollow channel extending within the main body and being in fluid communication with a chamber disposed within the main body; and
   a sensor insertable into the chamber, the sensor comprising a conductive material and a hydrogen selective material in contact with the conductive material, wherein the hydrogen selective material has a resistivity that increases in response to increased concentration of hydrogen, wherein the humidity control unit being disposed adjacent to the sensor is adapted to maintain a relative humidity for the sensor in a range from 0.1% to 15%, wherein the hydrogen selective material comprises polyaniline, wherein the polyaniline is doped with a dopant that increases pH sensitivity of the polyaniline, wherein the dopant comprises dinonylnapthylsulfonic acid, and wherein the polyaniline has a resistivity that increases in response to increased concentration of hydrogen;
   an analog front-end circuit;
   a microcontroller;
   a display; and
   a memory, wherein the display, the memory, and the analog front-end circuit are each electrically connected to the microcontroller.

9. A breath test method for screening for a gastrointestinal disorder, comprising the steps of:
   (a) providing a portable, hand-held breath analyzer, wherein the portable, hand-held breath analyzer comprises:
      (i) a main body connectable to a power source and having a processor, an electrical circuit, a humidity control unit, and a hollow channel extending within the main body and being in fluid communication with a chamber disposed within the main body, the chamber containing a sensor, the electrical circuit operably connecting the power source to the gas sensor and connecting the gas sensor to the processor; and
      (ii) a mouthpiece removably insertable into the channel such that the mouthpiece is in fluid communication with the chamber, wherein the sensor comprises a conductive material and a hydrogen selective material in contact with the conductive material, wherein the hydrogen selective material comprises polyaniline, wherein the polyaniline is doped with a dopant that increases pH sensitivity of the polyaniline, wherein the dopant comprises dinonylnapthylsulfonic acid, wherein the hydrogen selective material has a resistivity that increases in response to increased concentration of hydrogen;

(b) controlling humidity, by the humidity control unit, in an environment immediately surrounding the sensor such that the humidity is within a predetermined range, wherein the predetermined range of the humidity is from 0.1% to 15%;

(c) prompting a user to exhale a breath sample into the mouthpiece;

(d) allowing the processor to measure a resistivity of the sensor that occurs when the breath sample contacts the sensor; and (e) designating the user as having an increased likelihood of having a gastrointestinal disorder if the measured resistivity is above or beneath a predetermined value.

10. The breath test method of claim 9, wherein the gastrointestinal disorder is celiac disease.

11. The breath test method of claim 9, wherein the gastrointestinal disorder is non-celiac gluten sensitivity.

12. The breath test method of claim 9, wherein the gastrointestinal disorder is small intestinal bacterial overgrowth.

13. The breath test method of claim 9, wherein the gastrointestinal disorder is lactose intolerance.

14. The breath test method of claim 9, wherein the gastrointestinal disorder is fructose intolerance.

15. The breath test method of claim 9, wherein the sensor is configured to detect hydrogen gas in a concentration of between 1-100 ppm.

16. The breath test method of claim 9, wherein the predetermined range of humidity is from 3% to 7%.

17. A breath test method for diagnosing a gastrointestinal disorder, comprising the steps of:
(a) providing a portable, hand-held breath analyzer, wherein the portable, hand-held breath analyzer comprises:
  (i) a main body connectable to a power source and having a processor, an electrical circuit, a humidity control unit, and a hollow channel extending within the main body and being in fluid communication with a chamber disposed within the main body, the chamber containing a sensor that is disposed adjacent to the humidity control unit, the electrical circuit operably connecting the power source to the gas sensor and connecting the gas sensor to the processor; and
  (ii) a mouthpiece removably insertable into the channel such that the mouthpiece is in fluid communication with the chamber, wherein the sensor comprises a conductive material and a hydrogen selective material in contact with the conductive material, wherein the hydrogen selective material comprises polyaniline, wherein the polyaniline is doped with a dopant that increases pH sensitivity of the polyaniline, wherein the dopant comprises dinonylnapthylsulfonic acid, wherein the hydrogen selective material has a resistivity that increases in response to increased concentration of hydrogen;

(b) controlling humidity, by the humidity control unit, in an environment immediately surrounding the sensor such that the humidity is within a predetermined range, wherein the predetermined range of humidity is from 0.1% to 15%;

(c) prompting a user to exhale a breath sample into the removable mouthpiece;

(d) allowing the processor to measure a resistivity of the sensor that occurs when the breath sample contacts the sensor; and (e) diagnosing the user as having a gastrointestinal disorder if the measured resistivity is above and/or beneath a predetermined value.

18. The breath test method of claim 17, wherein the gastrointestinal disorder is celiac disease.

19. The breath test method of claim 17, wherein the gastrointestinal disorder is non-celiac gluten sensitivity.

* * * * *